US010111635B2

(12) United States Patent
Kato et al.

(10) Patent No.: US 10,111,635 B2
(45) Date of Patent: Oct. 30, 2018

(54) IMAGE PROCESSING APPARATUS, IMAGE PROCESSING METHOD, AND STORAGE MEDIUM

(71) Applicant: Toshiba Medical Systems Corporation, Otawara-shi (JP)

(72) Inventors: Mitsuaki Kato, Kawasaki (JP); Kenji Hirohata, Minato-ku (JP); Akira Kano, Kawasaki (JP); Shinya Higashi, Yokohama (JP); Shigeo Kaminaga, Otawara (JP); Yasuko Fujisawa, Nasushiobara (JP); Satoshi Wakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 70 days.

(21) Appl. No.: 15/285,044

(22) Filed: Oct. 4, 2016

(65) Prior Publication Data
US 2017/0095221 A1    Apr. 6, 2017

(30) Foreign Application Priority Data

Oct. 5, 2015   (JP) .................................. 2015-197887

(51) Int. Cl.
*G06K 9/00*   (2006.01)
*A61B 6/00*   (2006.01)
(Continued)

(52) U.S. Cl.
CPC ............ *A61B 6/5217* (2013.01); *A61B 6/032* (2013.01); *A61B 6/4417* (2013.01); *A61B 6/466* (2013.01);
(Continued)

(58) Field of Classification Search
CPC ....... A61B 6/517; A61B 6/032; A61B 6/4417; A61B 6/466; A61B 6/481; A61B 6/486;
(Continued)

(56) References Cited

U.S. PATENT DOCUMENTS 7,069,068 B1 *  6/2006  Ostergaard ............. A61B 5/055
                                                324/307
7,172,569 B2 *  2/2007  Kleinekofort ....... A61M 1/3663
                                                604/6.06
(Continued)

FOREIGN PATENT DOCUMENTS

JP    2008-241432    10/2008
JP    2009-195586     9/2009
(Continued)

OTHER PUBLICATIONS

Yoshimasa Kadooka "Heart Simulation Leading to Tailor-Made Treatment~Introduction of the world's most advanced heart simulator and its application" ITU Journal, vol. 41, No. 6,Jun. 2011, pp. 7 (with Partial English Translation).
(Continued)

*Primary Examiner* — Jose Couso
(74) *Attorney, Agent, or Firm* — Oblon, McClelland, Maier & Neustadt, L.L.P.

(57) ABSTRACT

An image processing apparatus according to an embodiment includes storage circuitry and processing circuitry. The storage circuitry stores therein fluid resistance data representing a correlation among a vascular shape, a blood flow rate, and a pressure loss. The processing circuitry extracts, from three-dimensional image data in which a blood vessel of a subject is rendered, vascular shape data representing a shape of the blood vessel. The processing circuitry performs fluid analysis based on the vascular shape data and the blood flow rate and the pressure loss that correspond to the vascular shape data and that are correlated by the fluid
(Continued)

resistance data to derive a functional index related to a blood circulation state in the blood vessel of the subject.

15 Claims, 14 Drawing Sheets

(51) Int. Cl.
*G06K 9/46* (2006.01)
*G06T 7/00* (2017.01)
*A61B 6/03* (2006.01)
*G06T 7/12* (2017.01)
*G16H 50/50* (2018.01)
*G06F 17/50* (2006.01)

(52) U.S. Cl.
CPC ............ *A61B 6/481* (2013.01); *A61B 6/486* (2013.01); *A61B 6/504* (2013.01); *A61B 6/507* (2013.01); *A61B 6/5235* (2013.01); *A61B 6/5247* (2013.01); *G06K 9/00577* (2013.01); *G06K 9/46* (2013.01); *G06K 9/4604* (2013.01); *G06T 7/0012* (2013.01); *G06T 7/0016* (2013.01); *G06T 7/12* (2017.01); *G16H 50/50* (2018.01); *A61B 6/5223* (2013.01); *G06F 17/5009* (2013.01); *G06F 2217/16* (2013.01); *G06K 2209/05* (2013.01); *G06T 2207/10012* (2013.01); *G06T 2207/10081* (2013.01); *G06T 2207/10088* (2013.01); *G06T 2207/10132* (2013.01); *G06T 2207/30104* (2013.01); *G06T 2207/30172* (2013.01)

(58) Field of Classification Search
CPC ......... A61B 6/503; A61B 6/504; A61B 6/507; A61B 6/5235; A61B 6/5247; A61B 5/0044; A61B 5/02; A61B 5/02007; A61B 5/02028; A61B 5/024; A61B 5/026; A61B 5/029; A61B 8/065; A61B 8/06; A61B 8/04; A61B 8/02; A61B 34/10; A61B 2576/023; G06T 7/12; G06T 7/0012; G06T 7/0016; G06T 11/00; G06T 17/00; G06T 2200/04; G06T 2210/41; G06T 2211/404; G06T 2207/10012; G06T 2207/10081; G06T 2207/10088; G06T 2207/0132; G06T 2207/30104; G06T 2207/30048; G06K 9/00577; G06K 9/4604; G06K 9/46; G06K 2009/4666; G06K 2209/05; G01R 33/5601; G01R 33/5635; G01R 33/56366; G01R 33/56308; A61M 5/007; A61M 1/3658; A61M 1/3639; A61M 1/3663; A61M 2205/3344; A61M 2205/3334; A61M 2205/50; G06F 19/3437; G06F 19/12; G06F 19/3431; G06F 17/5009; G06F 2217/16

See application file for complete search history.

(56) References Cited

U.S. PATENT DOCUMENTS

| | | | |
|---|---|---|---|
| 7,653,510 B2 | 1/2010 | Hirohata et al. | |
| 8,965,084 B2* | 2/2015 | Mihalef | G06F 19/3437 382/128 |
| 9,135,699 B2* | 9/2015 | Ralovich | G06T 7/0012 |
| 9,320,487 B2* | 4/2016 | Mittal | A61B 6/481 |
| 9,572,495 B2* | 2/2017 | Schmitt | A61B 5/0066 |
| 9,724,164 B2* | 8/2017 | Yagi | A61B 34/25 |
| 2005/0038346 A1* | 2/2005 | Miele | A61B 5/02028 600/485 |
| 2013/0132054 A1 | 5/2013 | Sharma et al. | |
| 2014/0249791 A1 | 9/2014 | Taylor et al. | |
| 2015/0032435 A1* | 1/2015 | Yagi | A61B 5/055 703/11 |
| 2016/0073970 A1* | 3/2016 | Sharma | A61B 6/507 600/431 |
| 2016/0367154 A1* | 12/2016 | Gladshtein | A61B 5/0261 |
| 2017/0032097 A1* | 2/2017 | Itu | G06F 19/3437 |
| 2017/0181642 A1* | 6/2017 | King | A61B 5/021 |

FOREIGN PATENT DOCUMENTS

| | | |
|---|---|---|
| JP | 2013-534154 A1 | 9/2013 |
| JP | 2014-534489 | 12/2014 |

OTHER PUBLICATIONS

James K. Min et al., "Rationale and design of the DeFACTO (Determination of Fractional Flow Reserve by Anatomic Computed Tomographic AngiOgraphy) study" Journal of Cardiovascular Computed Tomography, May 2011, pp. 9.

Matthias Renker et al., "Comparison of Diagnostic Value of a Novel Noninvasive Coronary Computed Tomography Angiography Method Versus Standard Coronary Angiography for Assessing Fractional Flow Reserve", The American Journal of Cardiology, 2014, pp. 6.

* cited by examiner

IMAGE PROCESSING APPARATUS, IMAGE PROCESSING METHOD, AND STORAGE MEDIUM

CROSS-REFERENCE TO RELATED APPLICATIONS

This application is based upon and claims the benefit of priority from Japanese Patent Application No. 2015-197887, filed on Oct. 5, 2015; the entire contents of which are incorporated herein by reference.

FIELD

Embodiments described herein relate generally to an image processing apparatus, an image processing method, and a storage medium.

BACKGROUND

Causes of ischemic diseases of organs are conventionally known to be roughly classified into hematogenous disorder and functional disorder of organs themselves. For hematogenous disorder, an evaluation index and a diagnostic technology to suggest a therapeutic strategy in a noninvasive manner has been sought after. Stenosis, which is an example of coronary hematogenous disorder, is a serious lesion leading to ischemic heart disease. For such ischemic heart disease, it is necessary to determine whether pharmacological treatment, stent treatment, or the like should be provided.

In recent years, measurement of fractional flow reserve (FFR) under guidewire control in coronary angiography (CAG) using catheters is being recommended for diagnosis with coronary hematogenous ischemic evaluation. However, for example, if coronary hematogenous ischemia can be evaluated with use of medical images of the heart collected by a medical image diagnostic apparatus, such as an X-ray computed tomography (CT) apparatus, a magnetic resonance imaging (MRI) apparatus, and an ultrasound diagnostic apparatus, the need of catheter surgery may be eliminated.

DETAILED DESCRIPTION

Figure 1:
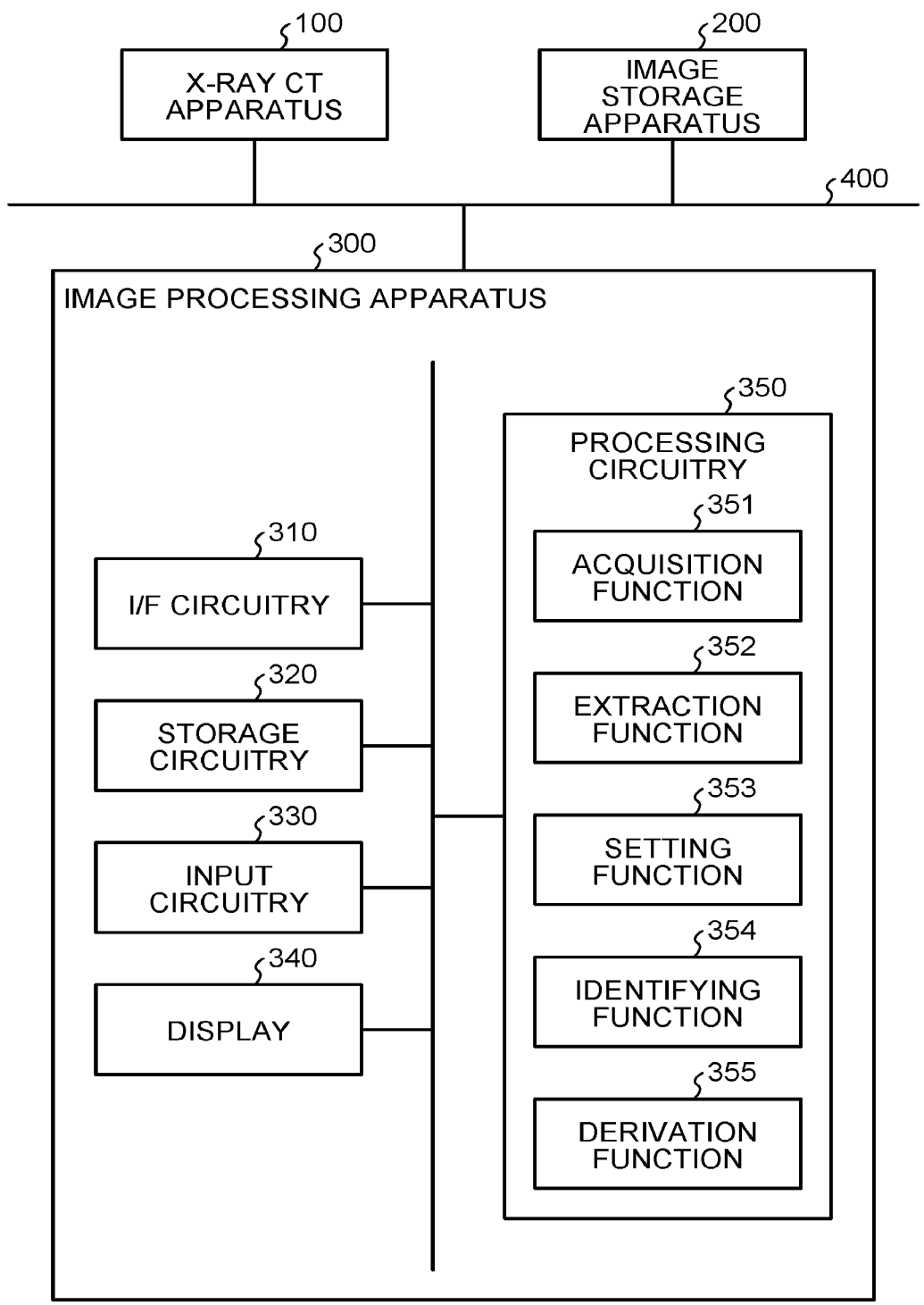
FIG. 1 is a diagram illustrating a configuration example of an image processing apparatus according to a first embodiment.

An image processing apparatus according to embodiments described herein includes storage circuitry and processing circuitry. The storage circuitry stores therein fluid resistance data representing a correlation among a vascular shape, a blood flow rate, and a pressure loss. The processing circuitry extracts, from three-dimensional image data in which a blood vessel of a subject is rendered, vascular shape data representing a shape of the blood vessel. The processing circuitry performs fluid analysis based on the vascular shape data and the blood flow rate and the pressure loss that correspond to the vascular shape data and that are correlated by the fluid resistance data to derive a functional index related to a blood circulation state in the blood vessel of the subject.

Referring to the accompanying drawings, an image processing apparatus, an image processing method, and a storage medium according to the embodiments are described in detail below.

First Embodiment

A first embodiment is now described. In the first embodiment, an example where a technology disclosed herein is applied to an image processing apparatus is described.

The image processing apparatus according to the first embodiment derives a functional index related to a blood circulation state of a blood vessel of a subject on the basis of time-series three-dimensional image data in which the blood vessel of the subject is rendered. An example where three-dimensional medical image data is used as the three-dimensional image data is described below. The case where blood vessels of the heart are subjected to analysis is described below as an example.

Examples of blood vessels of the heart include coronary arteries and an aorta. The coronary artery originates from the coronary artery origin in the aorta, runs on the myocardial surface to enter the endocardial side from the epicardial side. The coronary artery branches into innumerable capillaries on the tunica intima. The innumerable branched capillaries merge again to form vena cordis magna to be connected to the coronary sinus. The coronary vasculature has a feature in that perfusion needs to be ensured under dynamic changes of myocardial contraction and relaxation, unlike other organs.

Coronary blood flow is larger when perfusion pressure is reduced in left ventricular diastole than during systole where internal pressure at the coronary artery origin is increased due to mechanical blood flow constriction action by myocardial contraction. Thus, the blood flow velocity waveform of normal coronary arteries is a bimodal waveform with systole and diastole, and the blood flow in diastole is dominant. In contrast, it is known that anomalous blood flow waveforms are found depending on disease, for example, retrograde waves are found in systole for hypertrophic cardiomyopathy and aortic valve stenosis, and systolic anterograde waves are large for aortic regurgitation. Diastolic anterograde waveforms have a close relation to left ventricular diastolic function, in particular, left ventricular relaxation. In a left ventricular delayed relaxation example, there is a tendency that the peak of the diastolic waveform is delayed and the deceleration leg is moderate. In such disease, it is considered that diastolic coronary blood flow cannot be sufficiently increased during tachycardia, thus assisting myocardial ischemia.

Coronary blood flow occurs when coronary perfusion pressure equivalent to aortic pressure (that is, pressure at the aortic origin where coronary arteries are branched) is applied to the right and left coronary arteries branched from the aortic origin in anatomy. An important factor for determining the coronary blood flow is coronary vascular resistance as well as driving pressure that is aortic pressure. For example, it is known that a thick coronary blood vessel of 140 to 180 μm or more has approximately 20% of coronary vascular resistance and a microvessel of 100 to 150 μm or less has many of the remaining resistance components. Without what is called coronary stenosis, the resistance value thus depends on tonus of coronary microvessels.

Examples of factors of the coronary vascular resistance as used herein include vascular characteristics, arteriosclerosis, vascular stenosis, blood viscosity, and mechanical factors. The tonus for coronary microvessels is regulated by vascular characteristics, myocardial metabolism (myocardial oxygen consumption), neurohumoral factors, mechanical factors, various kinds of vasoactive substances as humoral factors, and blood viscosity. The tonus for coronary microvessels is also affected by various lesions including cardiomegaly and coronary arteriosclerosis to cause coronary circulatory disorder.

The coronary artery blood flow pulsation is affected by the pulsation pattern of the coronary artery blood flow, the control of the blood flow in the cardiac muscle with the cardiac muscle contraction, and reaction of the blood vessel in the cardiac muscle in response to mechanical stimulation. Examples of the order in which the blood flow is hindered by the cardiac muscle contraction include an increase in the cardiac muscle internal pressure, a change of the blood vessel capacity in the cardiac muscle, and oppression of the blood vessel in the cardiac muscle. The blood flow defining factors in the cardiac muscle diastole phase include the coronary artery pressure in the diastole phase, the blood vessel external force in the diastole phase, the heart rate, the ratio of the diastole phase with respect to the cardiac cycle, and the cardiac muscle relaxation.

The image processing apparatus according to the first embodiment derives, on the basis of the blood vessel or the like of the heart, a functional index related to a blood circulation state in the blood vessel. Examples of the functional index include an index of the function of the blood vessel related to stenosis. Specific examples of the functional index include a fractional flow reserve (FFR), a dynamic index in the blood vessel, a blood flow rate index, difference of FFR value, and stenosis value.

The FFR is expressed by Expression (1).

$$FFR = \frac{Pd - Pv}{Pa - Pv} \quad (1)$$

In the expression, Pa is pressure at the proximal stenosis, that is, on the aorta side across the stenosis, Pd is pressure at the distal stenosis, that is, on the opposite side to the aorta across the stenosis, and Pv is central venous pressure. The pressure Pa at the proximal stenosis may be an aorta pressure in the vicinity of the stenosis origin.

Dynamic indices in the blood vessel mean dynamic indices related to blood vessel walls and bloods. Examples of the dynamic indices related to blood vessel walls include an index related to a displacement of the blood vessel walls, an index related to stress or strain generated at the blood vessel walls, an index related to an internal pressure distribution imposed on the vascular lumen, and an index related to material characteristics representing vascular stiffness. Examples of the index related to material characteristics representing vascular stiffness include a mean inclination of a curve representing the relation between stress and strain in vascular tissue. Examples of the dynamic index include a pressure change between vasodilation and vasoconstriction, a pressure loss between before and after stenosis, and a pressure loss between the aorta region and the coronary artery region.

The blood flow rate index means an index of hemodynamics related to a blood flowing through a blood vessel. Examples of the blood flow rate index include a blood flow rate and a blood flow velocity. Other examples of the blood flow rate index include a blood flow rate change between vasodilatation and vasoconstriction and a flow rate ratio between coronary arteries (between stenosed coronary artery and nonstenosed coronary artery).

Conventionally, it has been difficult to easily obtain such a functional index. The conventional blood vessel structure and fluid analysis needs a large amount of analysis resources and long analysis time. In particular, a conventional method using three-dimensional structure and fluid simulation, which has a large calculation load, has a problem in that it takes a long time from the start of diagnosis to the provision of results. A conventional identification method using one-dimensional structure and fluid simulation, which provides boundary conditions for individual coronary arteries by the empirical rule, has a problem in that analysis accuracy is low.

In view of the above, the image processing apparatus according to the first embodiment is configured to derive a functional index of a blood vessel at high speed in a noninvasive or minimally invasive manner.

Specifically, the image processing apparatus stores therein fluid resistance data representing a correlation among a vascular shape, a blood flow rate, and a pressure loss. The image processing apparatus acquires, from time-series three-dimensional image data in which blood vessels of a subject are rendered, time-series vascular shape data representing the shape of the blood vessels. The image processing apparatus performs fluid analysis on the basis of the fluid resistance data and the time-series vascular shape data, thereby derivation a functional index related to a blood circulation state in the blood vessels of the subject.

The configuration of such an image processing apparatus is specifically described below. The following description is an example where time-series three-dimensional CT image data collected by an X-ray CT apparatus is used as time-series three-dimensional medical image data in which blood vessels of a subject are rendered. An example where an FFR is derived as a functional index is described below.

FIG. 1 is a diagram illustrating a configuration example of the image processing apparatus according to the first embodiment. For example, as illustrated in FIG. 1, an image processing apparatus 300 according to the first embodiment is connected to an X-ray computed tomography (CT) apparatus 100 and an image storage apparatus 200 via a network 400. The image processing apparatus 300 may be further connected to other medical image diagnostic apparatuses, such as an MRI apparatus, an ultrasound diagnostic apparatus, and a positron emission tomography (PET) apparatus, via the network 400.

The X-ray CT apparatus 100 collects CT image data of a subject. Specifically, the X-ray CT apparatus 100 rotationally moves an X-ray tube and an X-ray detector substantially around the subject, and detects an X-ray transmitted through the subject to collect projection data. Then, the X-ray CT apparatus 100 generates time-series three-dimensional CT image data on the basis of the collected projection data.

The image storage apparatus 200 stores therein image data collected by various kinds of medical image diagnostic apparatuses. For example, the image storage apparatus 200 is implemented by computer equipment such as a server apparatus. In the first embodiment, the image storage apparatus 200 acquires CT image data from the X-ray CT apparatus 100 via the network 400, and stores the acquired CT image data in storage circuitry provided inside or outside the image storage apparatus 200.

The image processing apparatus 300 acquires image data from various kinds of medical image diagnostic apparatuses via the network 400, and processes the acquired image data. For example, the image processing apparatus 300 is implemented by computer equipment such as a workstation. In the first embodiment, the image processing apparatus 300 acquires CT image data from the X-ray CT apparatus 100 or the image storage apparatus 200 via the network 400, and performs various kinds of image processing on the acquired CT image data. Then, the image processing apparatus 300 displays the CT image data before or after the image processing on a display or the like.

For example, as illustrated in FIG. 1, the image processing apparatus 300 includes interface (I/F) circuitry 310, storage circuitry 320, input circuitry 330, a display 340, and processing circuitry 350.

The I/F circuitry 310 is connected to the processing circuitry 350 to control transmission and communication of various kinds of data between the image processing apparatus 300 and various kinds of medical image diagnostic apparatuses or the image storage apparatus 200 connected via the network 400. For example, the I/F circuitry 310 is implemented by a network card, a network adapter, or a network interface controller (NIC). In the first embodiment, the I/F circuitry 310 receives CT image data from the X-ray CT apparatus 100 or the image storage apparatus 200, and outputs the received CT image data to the processing circuitry 350.

The storage circuitry 320 is connected to the processing circuitry 350 to store various kinds of data therein. For example, the storage circuitry 320 is implemented by a semiconductor memory element, such as a random access memory (RAM) or a flash memory, a hard disk, or an optical disc. In the first embodiment, the storage circuitry 320 stores therein CT image data received from the X-ray CT apparatus 100 or the image storage apparatus 200.

The input circuitry 330 is connected to the processing circuitry 350 to convert an input operation received from an operator into an electric signal and output the converted electric signal to the processing circuitry 350. For example, the input circuitry 330 is implemented by a trackball, a switch button, a mouse, a keyboard, or a touch panel.

The display 340 is connected to the processing circuitry 350 to display various kinds of information and various kinds of image data output from the processing circuitry 350. For example, the display 340 is implemented by a liquid crystal monitor, a cathode ray tube (CRT) monitor, or a touch panel.

The processing circuitry 350 controls each component of the image processing apparatus 300 in response to an input operation received from the operator via the input circuitry 330. For example, the processing circuitry 350 is implemented by a processor. In the first embodiment, the processing circuitry 350 stores CT image data output from the I/F circuitry 310 in the storage circuitry 320. The processing circuitry 350 reads CT image data from the storage circuitry 320, and displays the read CT image data on the display 340.

With the configuration described above, the storage circuitry 320 in the first embodiment stores therein correlation information and fluid resistance data. The storage circuitry 320 is an example of storage circuitry in the claims.

The correlation information is information representing a correlation between a physical index of a blood vessel and a functional index of the blood vessel related to a vascular blood circulation state. For example, the correlation information is created in advance on the basis of statistical data. The format of the correlation information may be a database, a table associated with values, a statistical model, a probabilistic model, or a mathematical model.

The blood vessel physical index is a physical index of the blood vessel. Examples of the physical index include a vascular cross-sectional shape variability index and a vascular resistance index. The vascular cross-sectional shape variability index is a variability index of the vascular cross-sectional shape from vasodilation to vasoconstriction or from vasoconstriction to vasodilation of the coronary blood vessel. Examples of the vascular cross-sectional shape variability index include a vascular cross-sectional shape variability index of the coronary artery and a vascular cross-sectional shape variability index of the aorta. The vascular resistance index is an index representing a relation between a pressure loss and a blood flow rate of the coronary artery. Examples of the vascular resistance index include a value obtained by dividing a pressure difference between the aorta (that is, the coronary ostium) and the coronary outlet by the square of the flow rate.

For example, the storage circuitry 320 stores therein correlation information representing a correlation between a vascular cross-sectional shape variability index and a pressure index, correlation information representing a correlation between a vascular resistance index and a flow rate index, and correlation information representing a correlation between the flow rate and the pressure loss. The kinds of vascular information are not limited thereto, and a correlation between other indices may be stored. The correlation information stored in the storage circuitry 320 is not limited to the exemplified ones, and other kinds of correlation information may be stored.

The storage circuitry 320 stores therein fluid resistance data representing a correlation among the vascular shape, the blood flow rate, and the pressure loss. For example, the fluid resistance data is created in advance from analysis results of three-dimensional fluid analysis performed on the basis of blood physical properties and a three-dimensional element model of blood vessels, results of an experiment performed by reproducing blood physical properties and vascular shapes and physical properties, or known analysis and experimental results. The format of the fluid resistance data may be a database, a table associated with values, a statistical model, a probabilistic model, or a mathematical model.

For example, the fluid resistance data stored in the storage circuitry 320 is created from analysis results of analysis using time-series three-dimensional image data in which the blood vessel is rendered. For example, the pressure loss included in the fluid resistance data is derived and set on the basis of a vascular cross-sectional shape variability index acquired from the time-series three-dimensional image data.

For example, the fluid resistance is expressed by Expression (2).

$$\Delta p = KQ^2 \qquad (2)$$

In the expression, K is the fluid resistance, Q is the flow rate, and $\Delta p$ is the pressure loss.

The fluid resistance depends on the vascular shape and the flow field. For example, when the vascular shape is a straight circular vessel and the flow field is a developed laminar flow, the fluid resistance K is expressed by Expression (3).

$$K = \frac{1}{2A^2} \rho \left(\frac{64}{Re}\right) \frac{L}{d} \qquad (3)$$

In the expression, A is the cross-sectional area of the lumen of the vessel, $\rho$ is the density, L is the length of the vessel, and d is the diameter of the vessel. Re is the Reynolds number, and is expressed by Expression (4).

$$Re = \frac{\mu u d}{\rho} \qquad (4)$$

In the expression, $\mu$ is the viscosity coefficient and u is the flow velocity in the blood vessel.

For example, in the fluid resistance data, the vascular shape is expressed by at least one element shape selected from an oval vessel, an expanding vessel, a constricted vessel, a curved vessel, a branch vessel, and a curved diffuser.

FIG. 2 to FIG. 5 are diagrams illustrating specific examples of element shapes representing vascular shapes and fluid resistance parameters for calculating the blood flow resistance in the fluid resistance data stored in the storage circuitry 320 according to the first embodiment.

Figure 2:
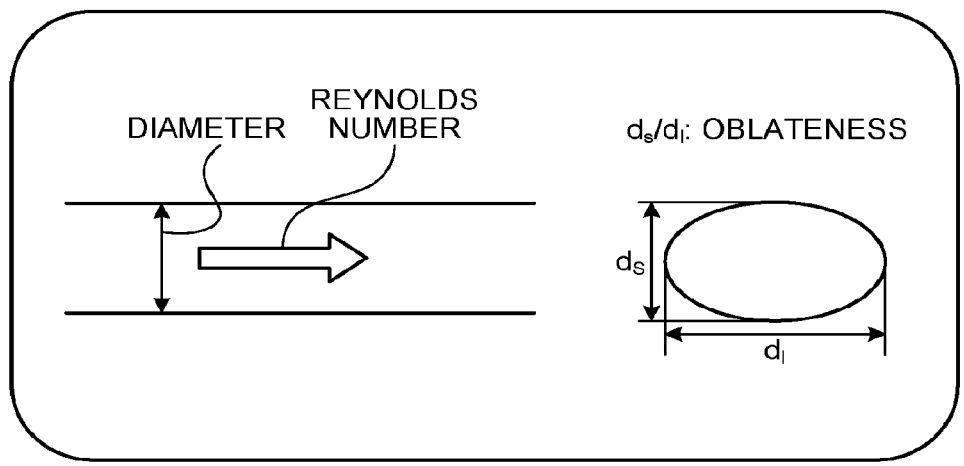
FIG. 2 to FIG. 5 are diagrams illustrating specific examples of element shapes representing vascular shapes and fluid resistance parameters representing vascular resistance in fluid resistance data stored in storage circuitry according to the first embodiment.

For example, as illustrated in FIG. 2, the vascular shape is represented by an oval element shape. In this case, for example, the element shape of the oval vessel includes the diameter, oblateness of the blood vessel, and Reynolds number as the fluid resistance parameters.

Figure 3:
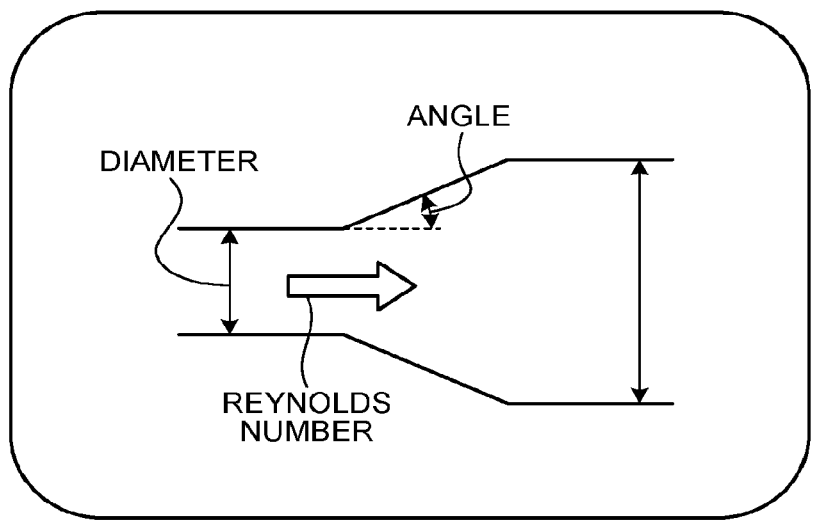

For another example, as illustrated in FIG. 3, the vascular shape is represented by an element shape of an expanding or constricted vessel. In this case, for example, the element shape of the expanding or constricted vessel includes the diameter of the inlet, the diameter of the outlet, the expanding or constricted angle, and the Reynolds number as the fluid resistance parameters.

Figure 4:
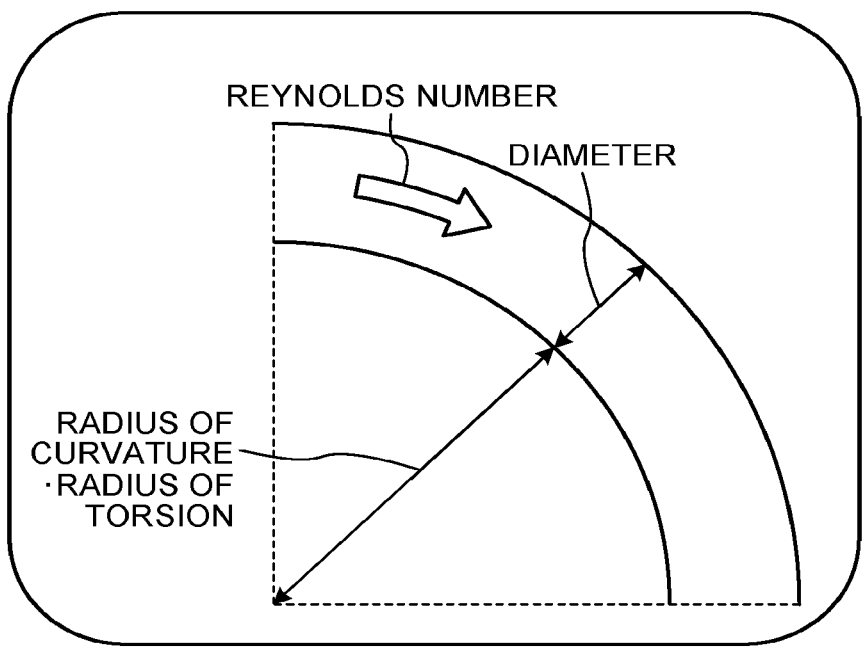

For another example, as illustrated in FIG. 4, the vascular shape is represented by an element shape of a curved vessel. In this case, for example, the element shape of the curved vessel includes the diameter, radius of curvature of the blood vessel, and Reynolds number as the fluid resistance parameters.

Figure 5:
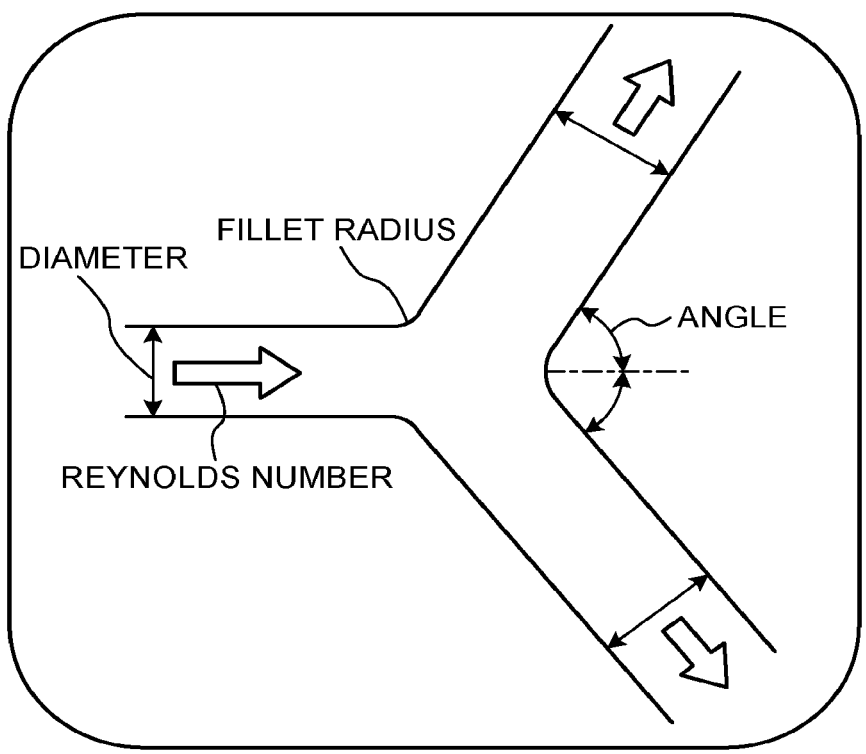

For another example, as illustrated in FIG. 5, the vascular shape is represented by an element shape of a branch vessel. The element shape of the branch vessel includes the diameter of each blood vessel, the branch angle, the fillet radius, the Reynolds number of the main stream, and the flow rate ratio in blood vessels.

The element shape representing the vascular shape is not limited to the exemplified ones, and may be other shapes such as a curved diffuser and a branch vessel with three or more branches.

For example, a mean shear stress $\tau$ in a cross-section that includes each point on the core line of the blood vessel and is perpendicular to the core line is determined by Expression (5).

$$\tau = \frac{d}{4} \frac{\Delta p}{L} \qquad (5)$$

With the fluid resistance data, registartion is performed so that various kinds of element shapes included in the fluid resistance data are changed in accordance with the shape of the blood vessel extracted from the three-dimensional CT image data. In this manner, the fluid resistance can be calculated from the thus obtained parameter values.

In FIG. 2 to FIG. 5, examples where one fluid resistance is saved for each element shape are described above, but any correlation and any physical quantity may be saved in any region in the element shape.

For example, the fluid resistance data includes, as the vascular shape, at least one of the cross-sectional area, the flow rate, the flow velocity, the static pressure, the dynamic pressure, the contrast agent concentration, the vorticity, the turbulent intensity, the mean value of shear stress, and coordinates in three-dimensional space for each point on the core line of the blood vessel.

For example, a distribution of the velocity, the pressure, the contrast agent concentration, or the like in a cross-section that includes each point on the core line of the blood vessel and is perpendicular to the core line may be saved.

Figure 6:
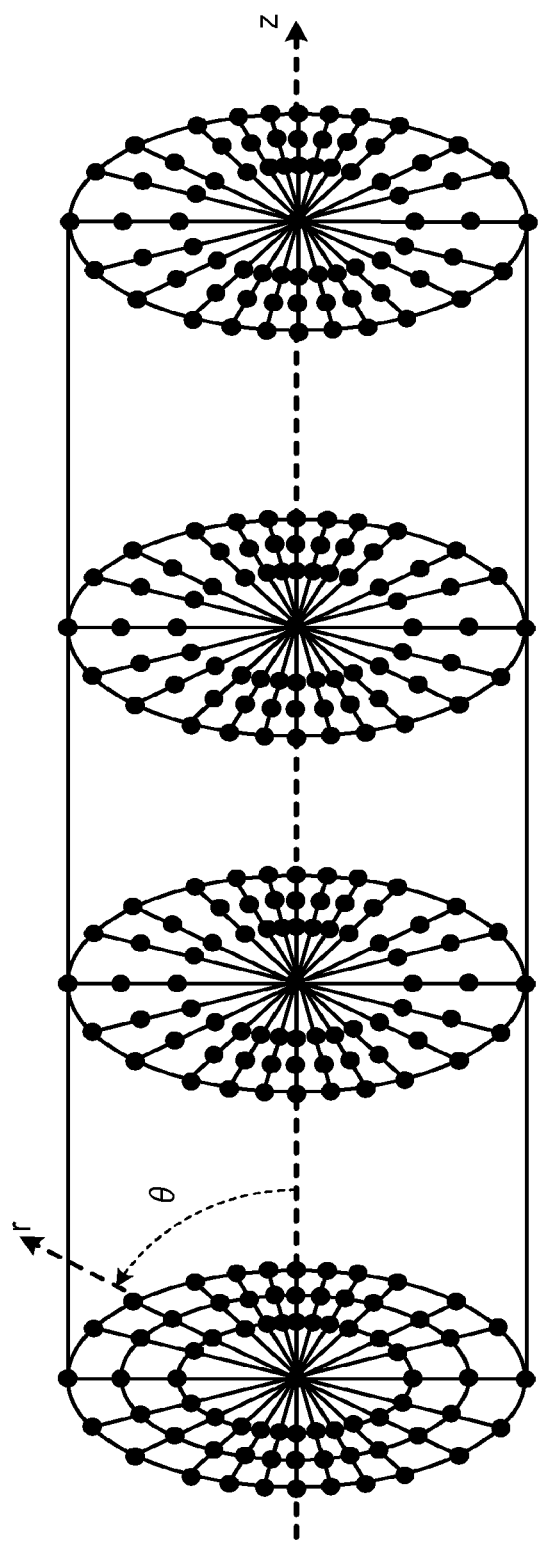
FIG. 6 and FIG. 7 are diagrams illustrating saving formats of the fluid resistance data stored in the storage circuitry according to the first embodiment.

Specifically, as illustrated in FIG. 6, the velocity, the pressure, the contrast agent concentration, or the like at each point forming a radial coordinate and an angular coordinate whose origin is on the core line in a cross-section that includes each point on the core line of the blood vessel and is perpendicular to the core line may be saved.

Figure 7:
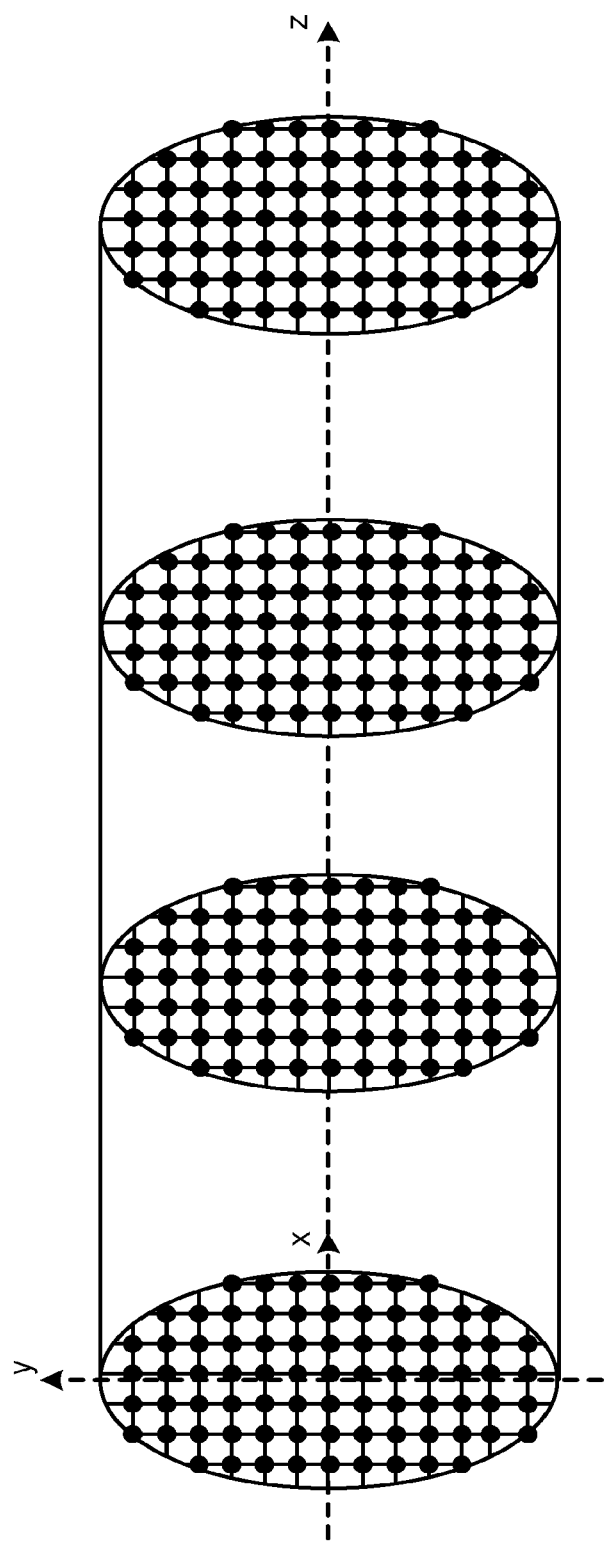

As illustrated in FIG. 7, the velocity, the pressure, the contrast agent concentration, or the like at each point forming coordinates represented by a first axis perpendicular to the core line of the blood vessel and a second axis perpendicular to the first axis in a cross-section perpendicular to the core line, in the cross-section that includes each point on the core line of the blood vessel and is perpendicular to the core line may be saved.

The use of the mean value in a cross-section that includes points on the core line of the blood vessel and is perpendicular to the core line enables the cross-sectional mean velocity in the core line direction, the pressure, the contrast agent concentration, and the like to be saved.

The use of values at points in the radial direction and the angular direction with each point on the core line in an inlet cross-section and an outlet cross-section of the blood vessel as the origin enables an input and output relation of the distribution of the flow velocity, the pressure, the contrast agent, or the like to be saved.

The use of values at points along the circumferential direction of the blood vessel inner wall in a cross-section that includes points on the core line of the blood vessel and is perpendicular to the core line enables the distribution of the wall shear stress or the like to be more accurately saved.

Various values can be saved by any other combination of coordinates, mean values, and integrated values.

For the blood viscosity, the Casson equation and various kinds of models, such as the Carreau-Yasuda model and the Herschel-Bulkley model, can be used.

Referring back to FIG. 1, the processing circuitry 350 in the first embodiment has an acquisition function 351, an extraction function 352, a setting function 353, an identifying function 354, and a derivation function 355. The processing circuitry 350 is an example of processing circuitry in the claims.

The acquisition function 351 acquires three-dimensional CT image data in which a blood vessel of a subject is rendered. For example, the acquisition function 351 acquires time-series three-dimensional CT image data in which a blood vessel of a subject is rendered. Specifically, the acquisition function 351 acquires three-dimensional CT image data from the X-ray CT apparatus 100 or the image storage apparatus 200 via the network 400, and stores the acquired three-dimensional CT image data in the storage circuitry 320.

The extraction function 352 extracts, from the three-dimensional image data in which the blood vessel of the subject is rendered, vascular shape data representing the shape of the blood vessel. For example, the extraction function 352 extracts time-series vascular shape data representing the shape of the blood vessel from the time-series three-dimensional CT image data acquired by the acquisition function 351. Specifically, the extraction function 352 reads the three-dimensional CT image data from the storage circuitry 320, and subjects the read three-dimensional CT image data to image processing, thereby extracting the vascular shape data.

For example, the extraction function 352 reads, from the time-series three-dimensional CT image data stored in the storage circuitry 320, three-dimensional CT image data corresponding to the range of cardiac phases of 70% to 100% in a ventricular diastolic region among phases of 0% to 100% of one heartbeat of the heart.

In this case, the extraction function 352 sets a functional index derivation target region in the vascular region included in the three-dimensional CT image data. Specifically, the extraction function 352 sets a derivation target region in the blood vessel region in response to an instruction made by the operator via the input circuitry 330 or image processing. Then, the extraction function 352 extracts the following pieces of information a) to m) from the three-dimensional CT image data as vascular shape data in the set derivation target region.

a) Blood vessel core line
b) Three-dimensional core coordinates
c) Distance from the origin of the blood vessel (the origin as used herein means a boundary between the heart and the aorta for the aorta and a boundary between the coronary artery and the aorta for the coronary artery)
d) Vascular cross-sectional area and luminal cross-sectional area in a cross-section perpendicular to the core line at respective core coordinates
e) Blood vessel inner wall coordinates and blood vessel outer wall coordinates in the circumferential direction in the cross-section perpendicular to the core line at respective core coordinates
f) Distance from the core line to the inner wall and distance from the core line to the outer wall in the circumferential direction in the cross-section perpendicular to the core line at respective core coordinates
g) Number of nodes of the blood vessel
h) Number of blood vessels sectioned by the node
i) Number of partitions of each blood vessel in the core line direction
j) Number of partitions of each blood vessel in the circumferential direction
k) Connection relation of blood vessels
l) Correspondence between the blood vessel and the blood vessel end
m) Number of ends of blood vessels The setting function 353 sets analysis conditions including blood physical properties, repeated calculation conditions, analysis initial values, and advance distribution as analysis conditions for the identifying function 354 and the derivation function 355, and eliminates blood vessels with a threshold radius or less, thereby reconstructing the connection relation of the blood vessels acquired by the extraction function 352.

Specifically, the setting function 353 sets the blood viscosity and density as physical properties of the blood. The setting function 353 sets the repetition maximum, the relaxation coefficient, and the residual tolerance in the repeated calculation as the repeated calculation conditions. The setting function 353 sets initial values of the flow rate, the static pressure, the fluid resistance, and the pressure boundary as the analysis initial values. The setting function 353 sets the cuff pressure, the time of one heartbeat, and the calculation position for branch angle and vascular diameter in a branch vessel. The setting function 353 sets the advance distribution of latent variables related to at least one of the shape or physical properties in a stress-free state in an identification target region. The advance distribution is used to calculate a predicted value of a blood flow rate index or a vascular morphology index in the identification target region. Various kinds of values used by the setting function 353 may be embedded in a system in advance, may be defined by an operator in an interactive manner, or may be set by using a part of the identifying function 354.

The setting function 353 eliminates a region with a threshold radius or less, where reliability is considered to be low, in the blood vessel acquired from the three-dimensional CT image data by the extraction function 352. It is desired that the threshold radius be set, for example, in the range from 1.0 to 0.5 mm on the basis of the CT resolution. The region to be eliminated is determined by starting a search from the downstream end of the coronary artery and determining the range from a point with a threshold radius therefrom to the downstream end of the blood vessel as the region to be eliminated. If every region in a blood vessel has a threshold radius or less or if a sufficient analysis region cannot be ensured in a blood vessel (such as 1 slice), the blood vessel is eliminated to reconstruct the connection structure of the blood vessel acquired by the extraction function 352.

The identifying function 354 identifies pressure boundary conditions at the end of the blood vessel, vascular deformation rigidity, and central venous pressure on the basis of three-dimensional CT image data. For example, the identifying function 354 identifies pressure boundary conditions at the end of the blood vessel, vascular deformation rigidity, and central venous pressure on the basis of time-series three-dimensional CT image data acquired by the acquisition function 351. For example, the identifying function 354 identifies pressure boundary conditions at the end of the blood vessel, vascular deformation rigidity, and central venous pressure on the basis of correlation information related to a vascular cross-sectional shape variability index and a pressure index and correlation information related to a vascular resistance index and a flow rate index stored in the storage circuitry 320 as well as fluid resistance that is a correlation between the flow rate and the pressure loss.

The identifying function 354 identifies, from the time-series three-dimensional CT image data acquired by the acquisition function 351, outlet pressure boundary conditions, vascular deformation rigidity, and central venous pressure in blood flow analysis for calculating an FFR. The identification method is as follows.

First, the identifying function 354 inputs time-series three-dimensional CT images acquired by the acquisition function 351, and uses image tracking technology to extract the time-dependent shape and deformation shape of the coronary artery vessel and the aortic vessel at the coronary artery origin. Then, the identifying function 354 calculates a vascular cross-sectional shape variability index from the extracted time-dependent shape and deformation data.

Next, the identifying function 354 performs fluid analysis and structural analysis based on Expressions (6) to (12) to identify the parameters by using parameter survey results related to the analysis conditions. Examples of the identification method include Bayesian hierarchical modeling using Markov chain Monte Carlo methods. The flow conservation law is expressed by Expression (6).

$$\frac{\partial \rho}{\partial t} + \nabla \cdot (\rho U) = 0 \tag{6}$$

In the expression, $\rho$ is the density and U is the flow velocity vector. The law of conservation of momentum is expressed by Expression (7).

$$\frac{\partial (\rho U)}{\partial t} + \nabla \cdot (\rho U \otimes U) = -\nabla p + \nabla \cdot \tau + S_M \tag{7}$$

In the expression, P is pressure, $\tau$ is strain rate, and $S_M$ is the momentum source term. The second term of the left side and the second term of the right side are expressed by Expressions (8) and (9).

$$\nabla \cdot (\rho U \otimes U) = \begin{bmatrix} \frac{\partial}{\partial x}(\rho U_x U_x) + \frac{\partial}{\partial y}(\rho U_y U_x) + \frac{\partial}{\partial z}(\rho U_z U_x) \\ \frac{\partial}{\partial x}(\rho U_x U_y) + \frac{\partial}{\partial y}(\rho U_y U_y) + \frac{\partial}{\partial z}(\rho U_z U_y) \\ \frac{\partial}{\partial x}(\rho U_x U_z) + \frac{\partial}{\partial y}(\rho U_y U_z) + \frac{\partial}{\partial z}(\rho U_z U_z) \end{bmatrix} \tag{8}$$

$$\tau = \mu \left( \nabla U + (\nabla U)^T - \frac{2}{3} \delta \nabla \cdot U \right) \tag{9}$$

The law of conservation of energy is expressed by Expressions (10) and (11).

$$\frac{\partial (\rho K)}{\partial t} + \nabla \cdot (\rho U K) = -U \cdot \nabla p + U \cdot (\nabla \cdot \tau) + U \cdot S_M \tag{10}$$

$$K = \frac{1}{2} U^2 \tag{11}$$

In the expression, K is kinetic energy and $U \cdot S_M$ represents the source term of momentum acting in response to vascular deformation. Expression (12) based on the following mechanics of materials proposed by Olufsen et al. is used as an approximate equation representing a relation among vasodilatory/vasoconstrictive deformation, rigidity, and pressure.

$$P - P_0 = 4Eh/3r_0 (1 - \sqrt{A_0/A}) \tag{12}$$

In the expression, P is pressure, $P_0$ is the pressure at a flow rate of 0, E is the elastic modulus, h is the thickness of the vascular wall, $r_0$ is the blood vessel radius at a flow rate of 0, $A_0$ is the vascular cross-sectional area at a flow rate of 0, and A is the vascular cross-sectional area. A blood vessel is made of super-elastic materials and has deformation characteristics with material anisotropy, and thus exhibits a non-linear deformation behavior due to a thickness change caused by axial stretch and large deformation. In order to take the deformation behavior into consideration, parameter survey may be performed in advance by using three-dimensional finite element analysis for anisotropic super-elastic material model parameters, h, r, $r_0$, axial displacement, and pressure P to create a response surface approximation for the rigidity E, thereby replacing the rigidity $4Eh/3r_0$ with the response surface approximation for correction.

In order to properly identify outlet pressure boundary conditions and vascular deformation rigidity, deformation information from vasodilatation to vasoconstriction of the coronary artery vessel at such a cardiac phase that is less affected by restriction from the myocardium is necessary. In view of this, a wave free period from a cardiac phase of around 70% in the vicinity of the peak flow rate of the coronary artery flow rate to a cardiac phase of 100% in the vasoconstrictive state is subjected to analysis. The central venous pressure Pv may be assumed to be a pressure at a blood flow rate of 0. The vascular elastic modulus, the blood pressure, and the blood viscosity and density may be determined by advance test information, such as a calcification index, vulnerability level index of a plaque, cuff pressure measurement, blood viscosity measurement, and blood density measurement, or may be identified by using the identifying function 354.

The derivation function 355 performs fluid analysis on the basis of fluid resistance data and vascular shape data to derive a functional index related to a blood circulation state in the blood vessel of the subject. For example, the derivation function 355 performs fluid analysis on the basis of the fluid resistance data stored in the storage circuitry 320 and the time-series vascular shape data acquired by the extraction function 352, thereby derivation a functional index related to the blood circulation state in the blood vessel of the subject. The derivation function 355 performs fluid analysis by using the boundary conditions identified by the identifying function 354 to derive a functional index.

Specifically, the derivation function 355 performs fluid analysis by using the analysis conditions set by the setting function 353. The derivation function 355 forms a vascular network on the basis of the core line, cross-sectional area, and connection information of the blood vessel included in the vascular shape data acquired by the extraction function 352, and performs fluid analysis by using the formed vascular network.

For example, analysis results necessary for coronary artery stenosis diagnosis are the flow rate in the blood vessel or the static pressure distribution on the core line, and the detailed three-dimensional distribution of the flow velocity or vortex are not necessary. In view of this, in the first embodiment, the derivation function 355 reduces the dimension of the vascular shape from the three-dimensional shape to the one-dimensional shape, and uses the correlation of the fluid resistance and the like as well, thereby achieving both of reduction in calculation load and high calculation accuracy.

Figure 8:
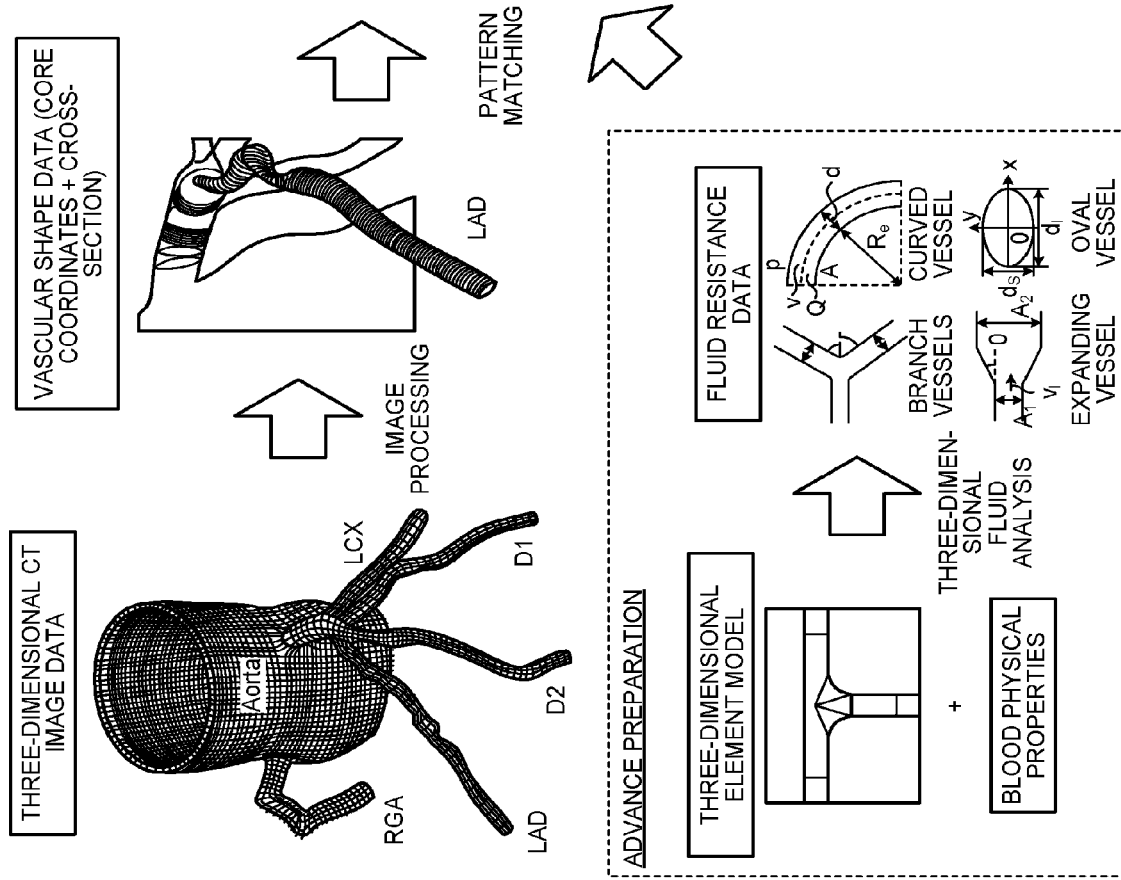
FIG. 8 is a diagram illustrating processing performed by a derivation function according to the first embodiment.

FIG. 8 is a diagram illustrating processing performed by the derivation function 355 according to the first embodiment. For example, as illustrated in FIG. 8, the derivation function 355 forms a vascular network by using the core line, cross-sectional area, and connection information of the blood vessel included in the vascular shape data acquired from the three-dimensional CT image data by the extraction function 352, thereby obtaining the one-dimensional coronary artery.

In this case, the derivation function 355 applies the following hypotheses in order to obtain one-dimensional governing equations.

1. The velocity distribution is substantially parallel to the core line.
2. The fluid is substantially steady in each phase of 70% to 100% of the pulsation of the heart.
3. The density and viscosity of the blood are substantially constant.

Expressions (13) and (14) are obtained from the hypotheses.

$$\frac{\partial Q}{\partial l} = 0 \tag{13}$$

$$\frac{\partial}{\partial l}\left(\frac{Q^2}{2A^2}\right) = -\frac{1}{\rho}\frac{\partial p}{\partial l} + \zeta\frac{Q^2}{2A^2} \tag{14}$$

In the expressions, Q is the flow rate, l is the distance of the blood vessel from the coronary artery origin, A is the cross-sectional area of the vascular lumen, p is the static pressure, $\rho$ is the density, and $\zeta$ is the loss coefficient.

Then, the derivation function 355 expresses the one-dimensional vascular shape as a vascular network. The derivation function 355 performs pattern matching between the vascular shape included in the fluid resistance data and the core line, cross-sectional area, and connection information of the blood vessel included in the vascular shape data, thereby applying the correlation represented by the fluid resistance data to the elements of the vascular network. Most of the correlations such as the fluid resistance depend on the value related to the flow field, such as the flow rate and pressure, and are reflected by sequentially substituting the flow rate or pressure obtained during convergence calculation of simultaneous equations to be described later.

Specifically, the derivation function 355 sets blood vessels, nodes, and boundaries that form a vascular network, thereby forming a vascular network. In this case, the derivation function 355 sets blood vessels and nodes that form a vascular network on the basis of the core line, cross-sectional area, and connection information of the blood vessel included in the vascular shape data. The derivation function 355 sets the static pressure identified by the identifying function 354 at the boundaries.

Figure 9:
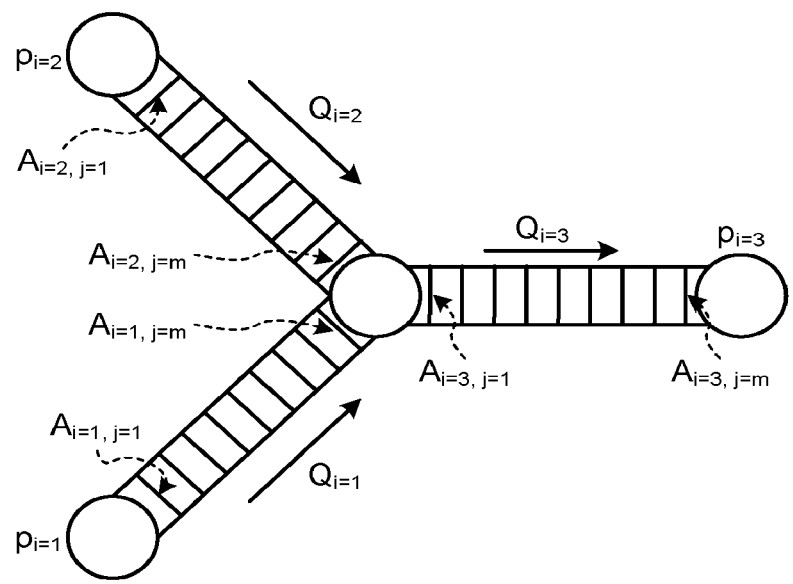
FIG. 9 is a diagram illustrating elements of a vascular network formed by a derivation function according to the first embodiment.

FIG. 9 is a diagram illustrating elements of a vascular network formed by the derivation function 355 according to the first embodiment. Circular elements illustrated at the center in FIG. 9 represent nodes of the blood vessel. Expression (13) is integrated with respect to the nodes to obtain Expression (15), and Expression (14) is integrated with respect to the nodes to obtain Expression (16).

$$\sum_{i=1}^{n} Q_i = 0 \tag{15}$$

$$\left(\frac{1}{2A_{i,l}^2} - \frac{1}{2A_{i,m}^2}\right)Q_i^2 + \frac{1}{\rho}(P_{i,l} - P_{i,m}) + \sum_{j=1}^{m}\left(\frac{\zeta_j}{2A_j^2}\right)Q_i^2 = 0 \tag{16}$$

In the expressions, n is the number of blood vessels connected to the node and m is the number of partitions of the blood vessel.

The derivation function 355 solves the simultaneous equations of Expressions (15) and (16) for each node and each blood vessel, thereby determine the flow rate of each blood vessel and the pressure distribution at the core lines. Then, the derivation function 355 derives an FFR from the determined flow rate and pressure distribution.

A description has been given of each processing function included in the processing circuitry 350. For example, the above-mentioned processing functions are stored in the storage circuitry 320 in the form of computer programs that can be executed by a computer. The processing circuitry 350 reads each computer program from the storage circuitry 320 and executes the read computer program to implement the processing function corresponding to each computer program. In other words, the processing circuitry 350 that has read each computer program has each processing function illustrated in FIG. 1.

In FIG. 1, a description has been given of an example where each processing function is implemented by the single processing circuitry 350, but the embodiments are not limited thereto. For example, the processing circuitry 350 may be configured by a combination of a plurality of independent processors, and each processing function may be implemented by each processor executing each computer program. Each processing function included in the processing circuitry 350 may be implemented in a manner that the processing functions are appropriately dispersed or integrated in a single processing circuit or a plurality of processing circuits.

Figure 10:
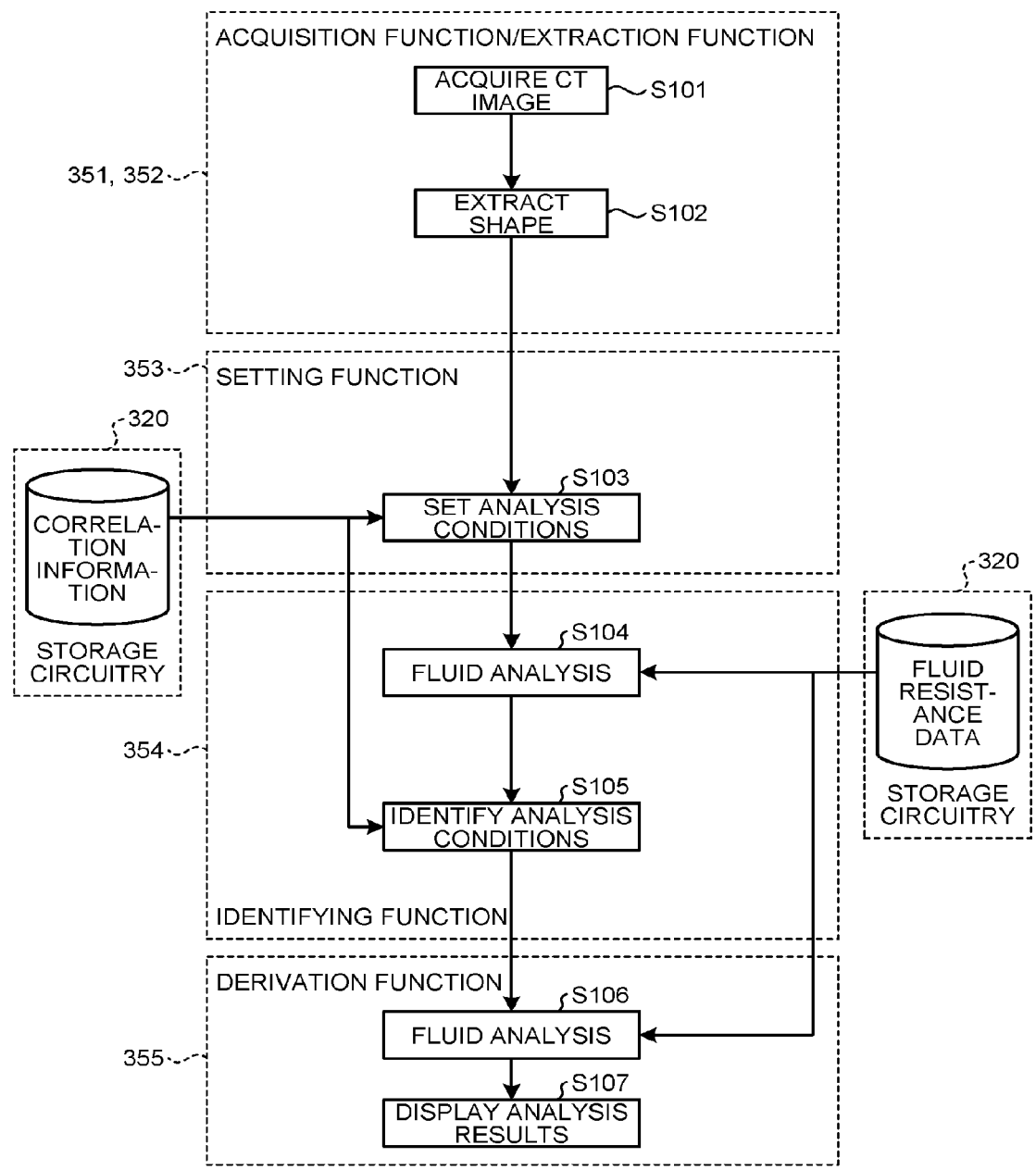
FIG. 10 is a flowchart illustrating the configuration of the image processing apparatus and a processing procedure of an image processing method according to the first embodiment.

FIG. 10 is a flowchart illustrating the configuration related to the image processing apparatus 300 and a processing procedure of an image processing method according to the first embodiment.

In the image processing apparatus 300 according to the first embodiment, first, the acquisition function 351 acquires time-series three-dimensional CT image data (Step S101). For example, Step S101 is implemented by the processing circuitry 350 calling and executing a predetermined computer program corresponding to the acquisition function 351 from the storage circuitry 320.

Subsequently, the extraction function 352 sets a functional index derivation target region to a blood vessel region included in the three-dimensional CT image data acquired by the acquisition function 351, and extracts vascular shape data on the set derivation target region (Step S102). For example, Step S102 is implemented by the processing circuitry 350 calling and executing a predetermined computer program corresponding to the extraction function 352 from the storage circuitry 320.

Subsequently, the setting function 353 sets analysis conditions for the identifying function 354 and the derivation function 355 (Step S103). Specifically, the setting function 353 sets the blood viscosity and density, the repetition maximum, the relaxation coefficient, and the residual tolerance in the repeated calculation, initial values of the flow rate, the static pressure, the fluid resistance, and the pressure boundary, the cuff pressure, the time of one heartbeat, the calculation position for branch angle and vascular diameter in a branch vessel, and the advance distribution of latent variables related to at least one of the shape and physical properties in a stress-free state in an identification target region. The advance distribution is used to calculate a predicted value of a blood flow rate index or a vascular morphology index in the identification target region. The setting function 353 eliminates a region with a threshold radius or less, where reliability is considered to be low, in the blood vessel acquired from the three-dimensional CT image data by the extraction function 352. It is desired that the threshold radius be set, for example, in the range from 1.0 to 0.5 mm on the basis of the CT resolution. The region to be eliminated is determined by starting a search from the downstream end of the coronary artery and determining the range from a point with a threshold radius therefrom to the downstream end of the blood vessel as the region to be eliminated. If every region in a blood vessel has a threshold radius or less or if a sufficient analysis region cannot be ensured in a blood vessel (such as 1 slice), the blood vessel is eliminated to reconstruct the connection structure of the blood vessel acquired by the extraction function 352. For example, Step S103 is implemented by the processing circuitry 350 calling and executing a predetermined computer program corresponding to the setting function 353 from the storage circuitry 320.

Subsequently, the identifying function 354 identifies pressure boundary conditions at the end of the blood vessel, vascular deformation rigidity, and central venous pressure on the basis of three-dimensional CT image data. In this case, the identifying function 354 performs fluid analysis with a plurality of static pressures as boundary conditions, and derives a correlation function for the flow rate and the fluid resistance (Step S104). Then, the identifying function 354 identifies the pressure boundary conditions at the end of the blood vessel, the vascular deformation rigidity, and the central venous pressure on the basis of the derived correlation function, the advanced correlation function, and the vascular shape variability index (Step S105). For example, Steps S104 and S105 are implemented by the processing circuitry 350 calling and executing a predetermined computer program corresponding to the identifying function 354 from the storage circuitry 320.

Subsequently, the derivation function 355 performs fluid analysis again on the basis of the identified boundary conditions to derive an FFR serving as a functional index (Step S106). Then, the derivation function 355 displays the derived FFR on the display 340 as analysis results (Step S107). For example, Steps S106 and S107 are implemented by the processing circuitry 350 calling and executing a predetermined computer program corresponding to the derivation function 355 from the storage circuitry 320.

Figure 11:
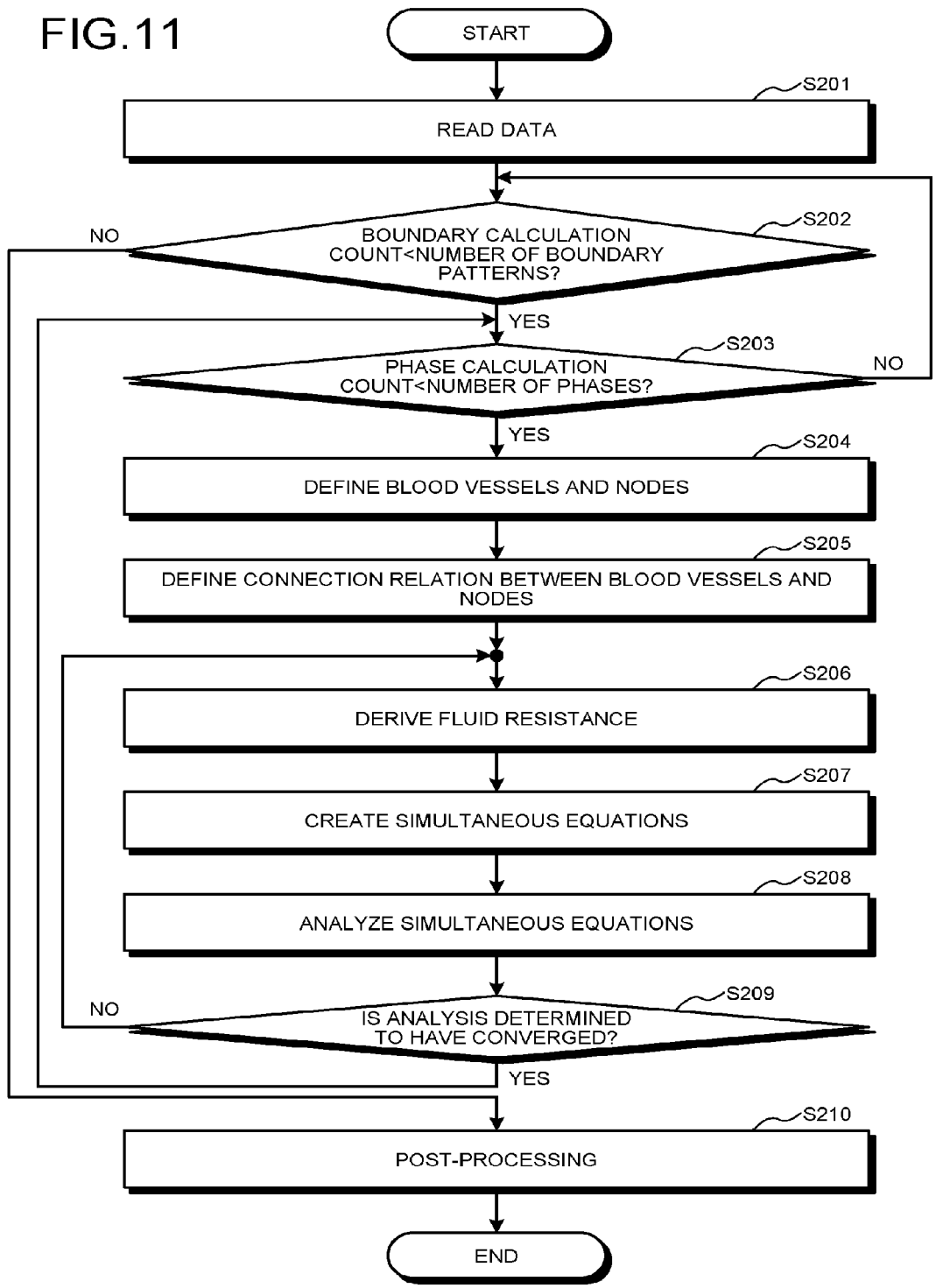
FIG. 11 is a flowchart illustrating a processing procedure of fluid analysis performed by the image processing apparatus according to the first embodiment.

FIG. 11 is a flowchart illustrating a processing procedure of fluid analysis performed by the image processing apparatus 300 according to the first embodiment. In the following description, the derivation function 355 performs fluid analysis. As described above, however, the identifying function 354 also performs fluid analysis by the same processing procedure. Each step described below is implemented by the processing circuitry 350 calling and executing a predetermined computer program corresponding to the identifying function 354 or the derivation function 355 from the storage circuitry 320.

First, the derivation function 355 reads vascular shape data, such as core coordinates and cross-sections, static pressure at the blood vessel end as boundary conditions, correspondence between the vascular shape and the element shape, and fluid resistance data (Step S201).

Subsequently, the derivation function 355 enters a loop of boundary calculation (Step S202, Yes). When the boundary calculation count becomes equal to or more than the number of boundary patterns of the boundary conditions (Step S202, No), the derivation function 355 exits the loop.

The derivation function 355 enters a loop of phase calculation (Step S203, Yes). When the phase calculation count becomes equal to or more than the number of phases (Step S203, No), the derivation function 355 exits the loop to proceed to the next boundary analysis (return to Step S202).

The derivation function 355 defines blood vessels and nodes (Step S204), and defines a connection relation between the blood vessels and the nodes (Step S205), thereby forming a vascular network.

The derivation function 355 derives a fluid resistance at the calculated flow velocity (Step S206) to create simultaneous equations (Step S207). The derivation function 355 analyzes the simultaneous equations (Step S208). When an error in the flow rate or the static pressure falls within a tolerable range, the derivation function 355 determines that the analysis has converged (Step S209, Yes), and proceeds to analysis of the next phase (returns to Step S203). Unless the analysis converges (Step S209, No), the derivation function 355 repeats the flow from the derivation of the fluid resistance to the analysis of the simultaneous equations (returns to Step S206).

After analysis is completed for every boundary, the derivation function 355 proceeds to post-processing, such as the displaying of analysis results (Step S210).

The inventors of the present invention found the fact that three-dimensional fluid analysis has very large calculation load and that one-dimensional fluid analysis has insufficient accuracy. To address the fact, as described above, the image processing apparatus 300 according to the first embodiment uses a fluid resistance database to perform one-dimensional fluid analysis that takes three-dimensional physical phenomena into consideration to derive a functional index in a derivation target region.

For example, it takes long time (for example, 12 hours or longer) for the conventional structural fluid analysis in some cases. In contrast, the image processing apparatus 300 according to the first embodiment uses a fluid resistance database, which can simplify at least one step (processing) among a plurality of pieces of processing for identifying a functional index.

Consequently, according to the first embodiment, the functional index of the blood vessel can be derived at high speed in a noninvasive or minimally invasive manner.

The case where a functional index is derived from time-series three-dimensional data is described in the above-mentioned example, but the embodiments are not limited thereto. For example, a functional index may be derived from three-dimensional data with one time phase.

In this case, the acquisition function 351 acquires three-dimensional CT image data with one cardiac phase in which a blood vessel of a subject is rendered. For example, said one cardiac phase to be processed is a cardiac phase in which the motion of the coronary artery becomes minimum, and the cardiac phase may be automatically set based on the shift amount of the coronary artery in a heartbeat or may be selected and set by an operator. For example, the acquisition function 351 acquires vascular shape data on a single cardiac phase that is determined in advance from cardiac phases of 70% to 100% in a ventricular diastolic region. The extraction function 352 extracts vascular shape data from the three-dimensional CT image data with one cardiac phase acquired by the acquisition function 351. The obtained vascular shape data may be data of whole of the coronary artery, data of either a right or left coronary artery, or data of a selected branch.

The identifying function 354 identifies pressure boundary conditions at the end of the blood vessel, vascular deformation rigidity, central venous pressure, and the like on the basis of the three-dimensional CT image data with one cardiac phase acquired by the acquisition function 351. For example, the identifying function 354 identifies outlet pressure boundary conditions, vascular deformation rigidity, and central venous pressure in blood flow analysis for calculating an FFR on the basis of the three-dimensional CT image data with one cardiac phase.

The derivation function 355 performs fluid analysis on the basis of the fluid resistance data and the vascular shape data with one cardiac phase extracted by the extraction function 352 to derive a functional index related to a blood circulation state in the blood vessel of the subject. For example, the derivation function 355 performs fluid analysis on the basis of the fluid resistance data stored in the storage circuitry 320 and the vascular shape data with one cardiac phase acquired by the extraction function 352 to derive a functional index related to a blood circulation state in the blood vessel of the subject. In this case, for example, the derivation function 355 derives a functional index by using, as analysis conditions, such an appropriate initial value of pressure loss that repeated calculation in fluid analysis converges on the basis of the vascular shape and the blood flow rate.

The image processing apparatus may further perform contrast agent concentration analysis. Examples where the image processing apparatus further performs a contrast agent concentration analysis are described as second to fifth embodiments.

In this case, the image processing apparatus includes an extraction unit configured to analyze, on the basis of time-series three-dimensional image data in which a blood vessel of a subject is rendered, a change in a contrast agent concentration in the blood vessel to calculate the flow velocity in the blood vessel.

Second Embodiment

Next, a second embodiment is described. The configuration of an image processing apparatus according to the second embodiment is basically the same as the configuration of the image processing apparatus 300 illustrated in FIG. 1. Therefore, the difference from the image processing apparatus 300 according to the first embodiment is mainly described below, and the components having the same roles as the components illustrated in FIG. 1 are denoted by the same reference symbols to omit detailed descriptions thereof.

Figure 12:
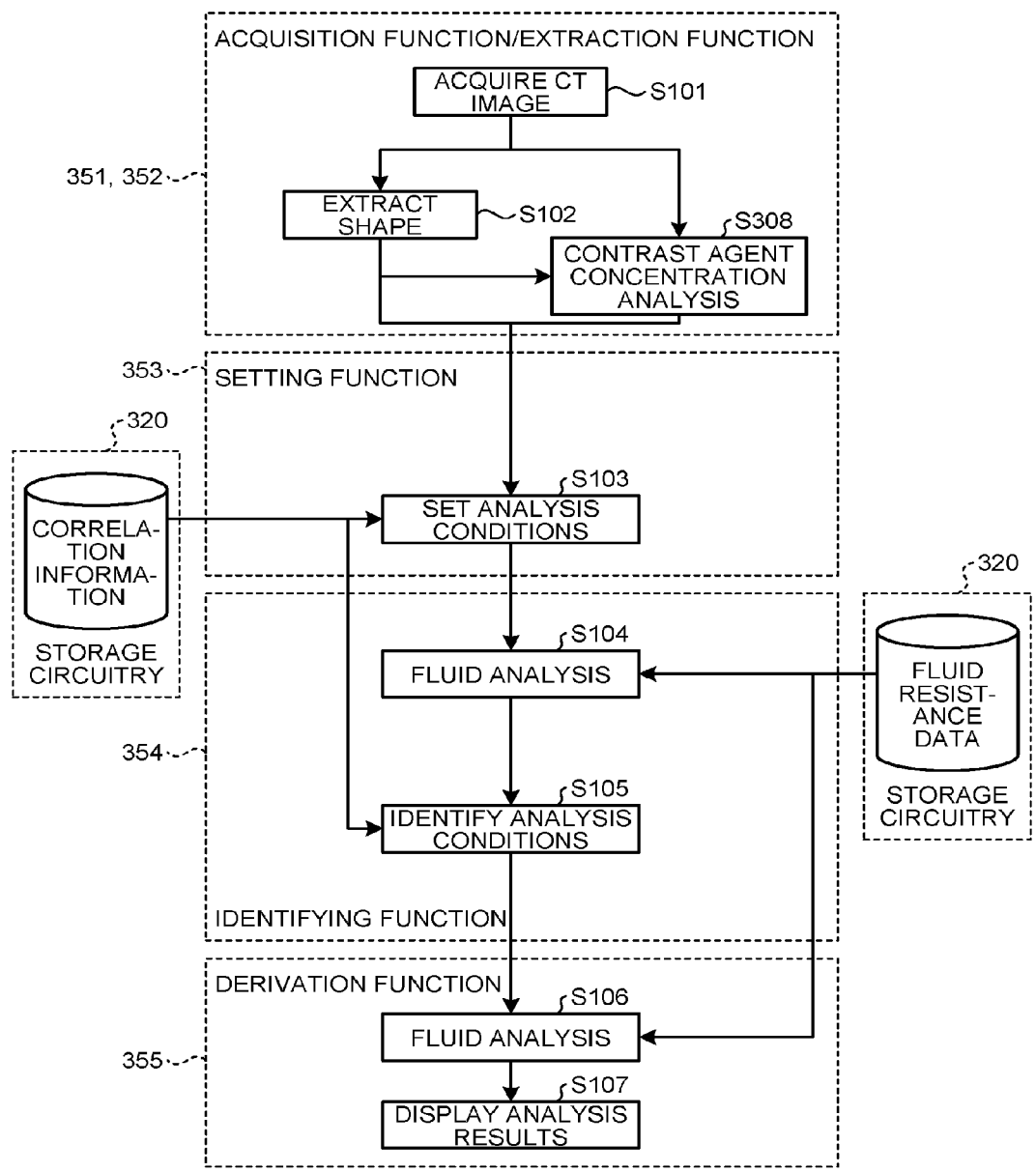
FIG. 12 is a flowchart illustrating a configuration of an image processing apparatus and a processing procedure of an image processing method according to a second embodiment.

FIG. 12 is a flowchart illustrating the configuration of an image processing apparatus 300 and a processing procedure of an image processing method according to the second embodiment.

For example, as illustrated in FIG. 12, the extraction function 352 in the second embodiment further analyzes, on the basis of three-dimensional CT image data acquired by the acquisition function 351, a change in a contrast agent concentration in a blood vessel to calculate the flow velocity in the blood vessel (Step S308).

Specifically, the extraction function 352 acquires, on the basis of time-series three-dimensional CT image data acquired by the acquisition function 351 and vascular shape data extracted from the three-dimensional CT image data, the flow velocity of the blood in each blood vessel by using physical relational expressions.

For example, the extraction function 352 calculates a local flow velocity by Expression (17) on the basis of a temporal gradient and a spatial gradient.

$$u = -\frac{\frac{\partial Y}{\partial t}}{\frac{\partial Y}{\partial x}} \qquad (17)$$

In the expression, u is the blood flow velocity, t is time, x is the position in the blood vessel, and Y is the contrast agent concentration.

The temporal gradient is obtained by dividing a concentration difference at different times at the position in the target blood vessel by the time difference. The spatial gradient is obtained by dividing a difference in concentration at positions across the region in the target blood vessel by the distance between the positions. The determination of the gradients amplifies noise included in the three-dimensional CT image data, but by removing a site with large noise, a highly reliable flow velocity can be obtained.

For example, the extraction function 352 calculates a mean flow velocity $u_m$ of the blood vessel cross-section by Expression (18).

$$u_m = -\frac{\frac{\partial (AY_m)}{\partial t}}{\frac{\partial (AY_m)}{\partial x}} \qquad (18)$$

In the expression, A is the cross-sectional area of the blood vessel and $Y_m$ is the mean contrast agent concentration in the cross-section.

The temporal gradient and the spatial gradient can be discretized by any method. For example, the extraction function 352 uses the central differences in time and phase to calculate a mean flow velocity at the i-th core coordinates and the n-th phase by using Expression (19).

$$u_{mi}^n = -\frac{(AY_m)_i^{n+1} - (AY_m)_i^{n-1}}{t^{n+1} - t^{n-1}} \bigg/ \frac{(AY_m)_{i+1}^n - (AY_m)_{i-1}^n}{x_{i+1} - x_{i-1}} \qquad (19)$$

The thus obtained mean flow velocity can be converted into the flow rate by using Expression (20).

$$Q = Au_m \qquad (20)$$

Then, in the second embodiment, the derivation function 355 performs fluid analysis by further using the flow rate obtained from the flow velocity in the blood vessel calculated by the extraction function 352.

The derivation function 355 applies the flow rate obtained from the contrast agent concentration together with the static pressure at the blood vessel end identified by the identifying function 354 to a highly reliable blood vessel. In this manner, the accuracy improvement and calculation time reduction in fluid analysis can be expected.

Various methods are conceivable for the application of the flow rate, such as a method of fixing the flow rate in a highly reliable blood vessel and a method of using the flow rate as an initial value for fluid analysis.

For example, Expression (21) is derived at regions having the same temporal gradient of the concentration.

$$\frac{\partial}{\partial x}\left\{u\left(\frac{\partial Y}{\partial x}\right)\right\} = 0 \quad (21)$$

This expression means that the product of the flow velocity and the spatial gradient of the contrast agent concentration is constant on the streamline. This expression is spatially integrated over the bifurcation of blood vessels in the tubular axis direction to obtain Expression (22).

$$u_n = \left[\sum_{j=1}^{n-1}\left\{A_j u_j\left(\frac{\partial Y}{\partial x}\right)_j\right\} - A_m u_m\left(\frac{\partial Y}{\partial x}\right)_m\right] \Big/ \left\{A_n\left(\frac{\partial Y}{\partial x}\right)_n\right\} \quad (22)$$

In the expression, u is the flow velocity in the blood vessel, x is the position in the blood vessel, A is the cross-sectional area of the blood vessel, Y is a contrast agent concentration, m is a number of the blood vessel serving as a main vessel, and n is the number of branch vessels connected to the main vessel. Furthermore, "j=1 to n" represents a plurality of branched blood vessels. It is understood from Expression (22) that the flow velocity in a target blood vessel can be acquired from the cross-sectional area, the flow velocity, and the spatial gradient of the contrast agent concentration of another blood vessel.

The derivation function 355 uses both of the flow velocity calculated by Expression (18) or (22), the flow conservation law, and the like. In this manner, the flow rate of each blood vessel can be more accurately determined.

According to the above-mentioned second embodiment, an FFR can be derived from the contrast agent concentration even when the flow rates in some blood vessels cannot be acquired or the flow rate analysis accuracy is low.

The configuration described above enables a functional index of blood vessels to be derived at high speed in a noninvasive or minimally invasive manner in the second embodiment similarly to the first embodiment.

Third Embodiment

Next, a third embodiment is described. The configuration of an image processing apparatus according to the third embodiment is basically the same as the configuration of the image processing apparatus 300 illustrated in FIG. 1. Therefore, the difference from the image processing apparatus 300 according to the first embodiment is mainly described below, and the components having the same roles as the components illustrated in FIG. 1 are denoted by the same reference symbols to omit detailed descriptions thereof.

Figure 13:
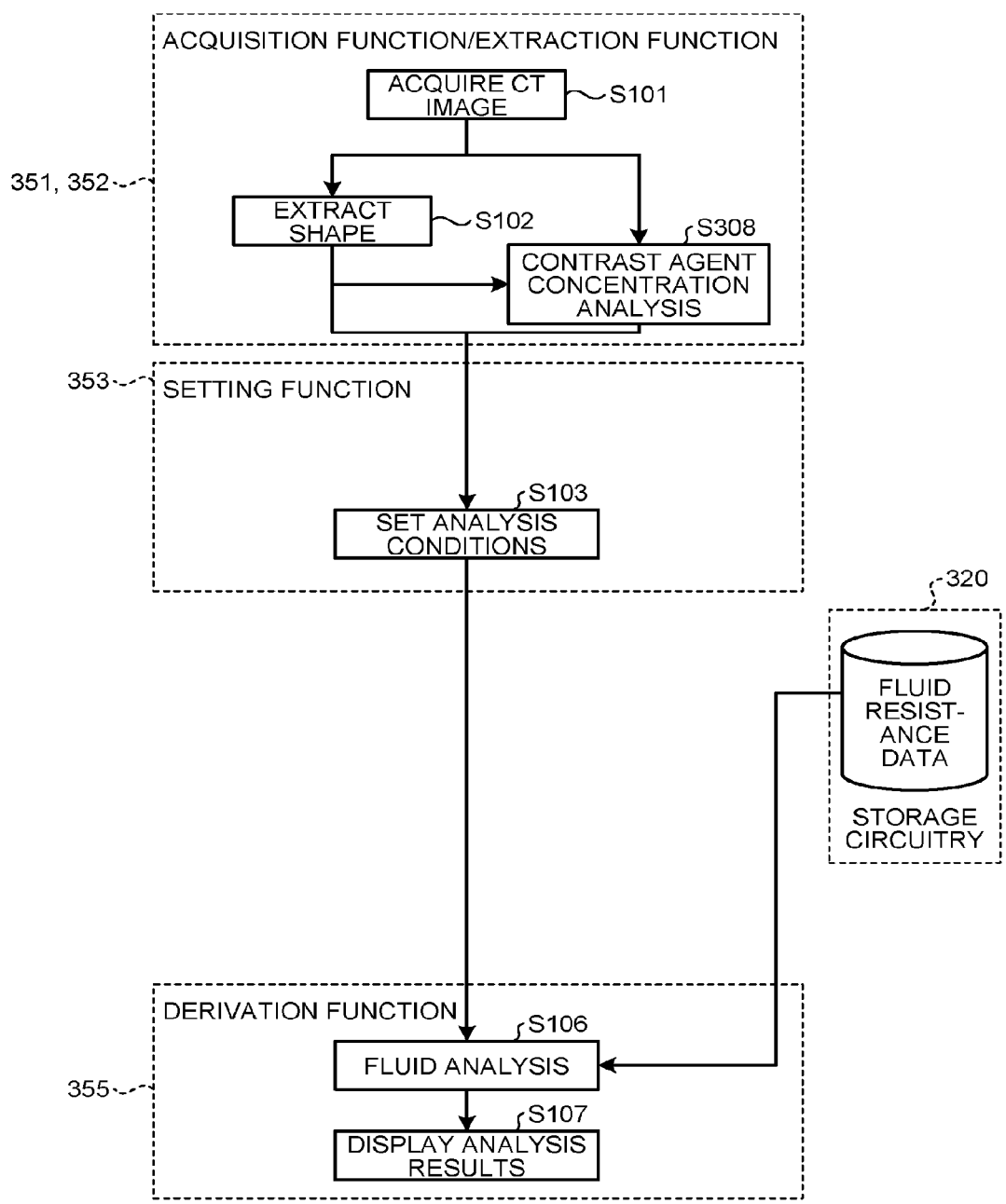
FIG. 13 is a flowchart illustrating a configuration of an image processing apparatus and a processing procedure of an image processing method according to a third embodiment.

FIG. 13 is a flowchart illustrating the configuration related to an image processing apparatus 300 and a processing procedure of an image processing method according to the third embodiment.

For example, as illustrated in FIG. 13, the configuration of the image processing apparatus according to the third embodiment is obtained by removing the identifying function 354 from the functions of the processing circuitry 350 in the configuration of the image processing apparatus 300 illustrated in FIG. 12.

For example, in the case where the flow rates of all the blood vessels can be accurately derived from the contrast agent concentration, the identifying function 354 can be omitted to derive an FFR as illustrated in FIG. 13. In this case, the boundary conditions for fluid analysis are the flow rate of each blood vessel, and the static pressure is derived through analysis.

The configuration described above enables a functional index of blood vessels to be derived at high speed in a noninvasive or minimally invasive manner in the third embodiment similarly to the first or the second embodiment.

Fourth Embodiment

Next, a fourth embodiment is described. The configuration of an image processing apparatus according to the fourth embodiment is basically the same as the configuration of the image processing apparatus 300 illustrated in FIG. 1. Therefore, the difference from the image processing apparatus 300 according to the first embodiment is mainly described below, and the components having the same roles as the components illustrated in FIG. 1 are denoted by the same reference symbols to omit detailed descriptions thereof.

Figure 14:
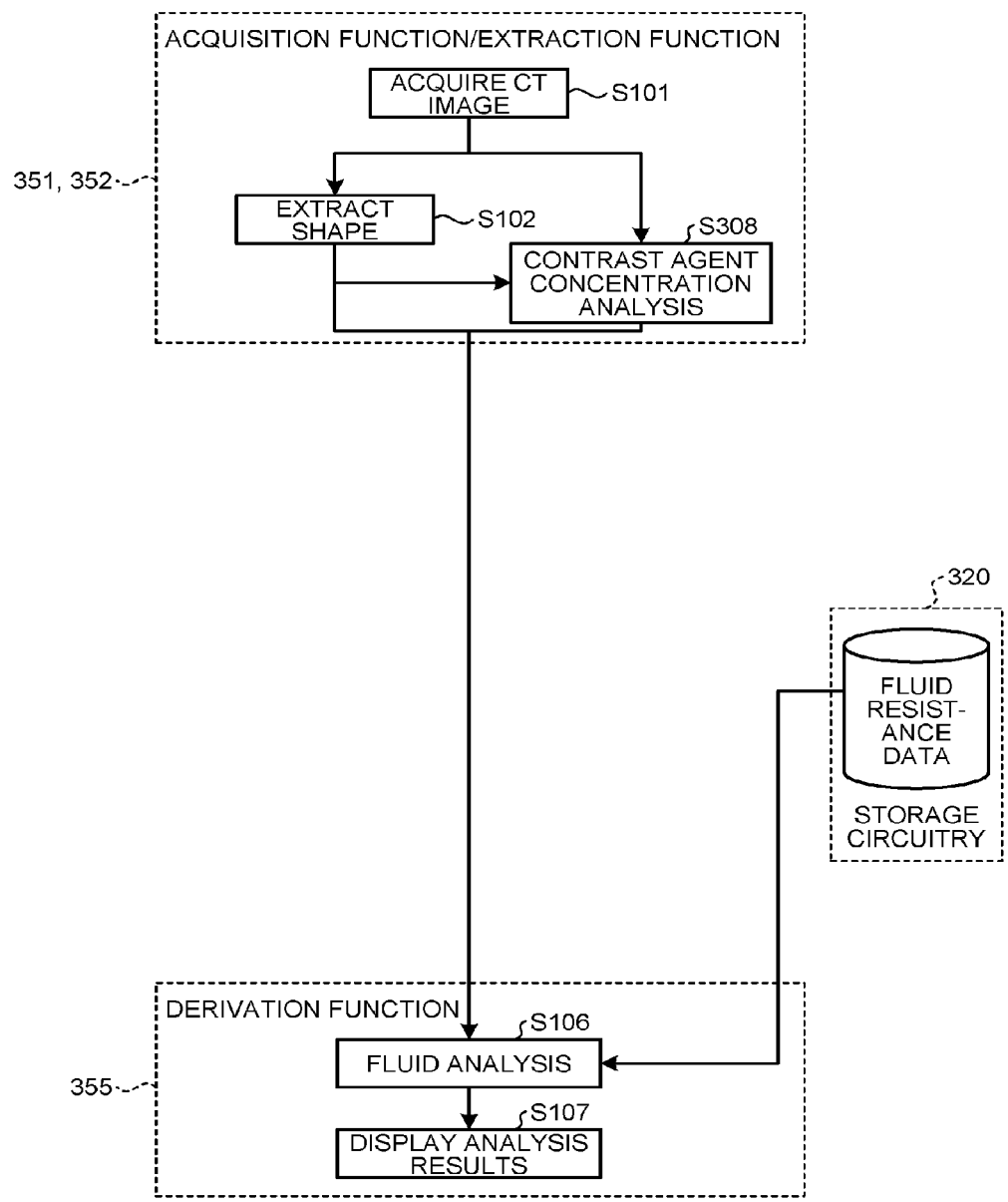
FIG. 14 is a flowchart illustrating a configuration of an image processing apparatus and a processing procedure of an image processing method according to a fourth embodiment.

FIG. 14 is a flowchart illustrating the configuration related to an image processing apparatus 300 and a processing procedure of an image processing method according to the fourth embodiment.

For example, as illustrated in FIG. 14, the configuration of the image processing apparatus according to the fourth embodiment is obtained by removing the setting function 353 and the identifying function 354 from the functions of the processing circuitry 350 in the configuration of the image processing apparatus 300 illustrated in FIG. 12.

For example, in the case where the vascular shape in every phase obtained from three-dimensional CT image data is clearly rendered, the setting function 353 and the identifying function 354 can be omitted to derive an FFR as illustrated in FIG. 14.

The configuration described above enables a functional index of blood vessels to be derived at high speed in a noninvasive or minimally invasive manner in the fourth embodiment similarly to the first or the second embodiment.

Fifth Embodiment

Next, a fifth embodiment is described. The configuration of an image processing apparatus according to the fifth embodiment is basically the same as the configuration of the image processing apparatus 300 illustrated in FIG. 1. Therefore, the difference from the image processing apparatus 300 according to the first embodiment is mainly described below, and the components having the same roles as the components illustrated in FIG. 1 are denoted by the same reference symbols to omit detailed descriptions thereof.

Figure 15:
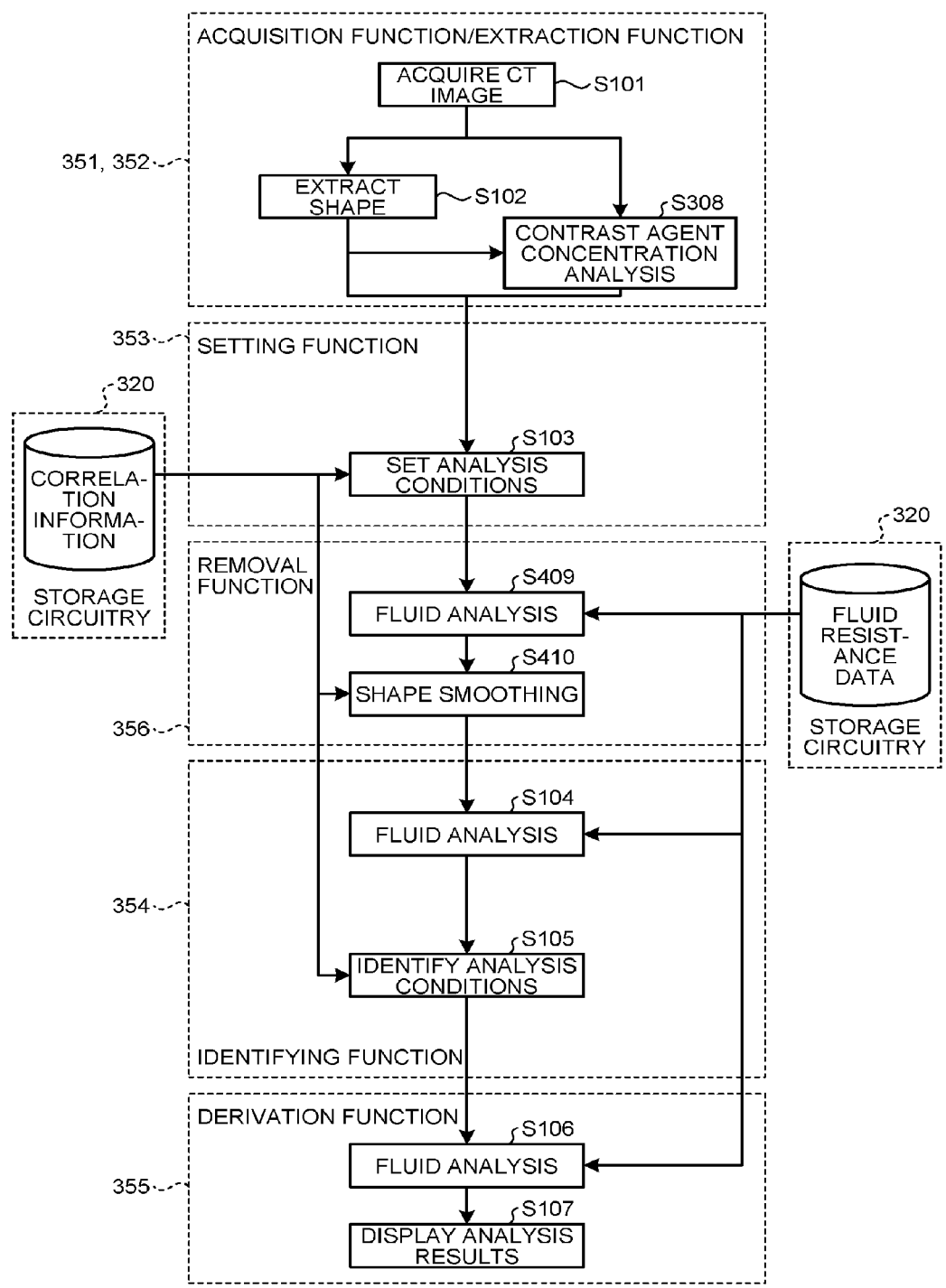
FIG. 15 is a flowchart illustrating a configuration of an image processing apparatus and a processing procedure of an image processing method according to a fifth embodiment.

FIG. 15 is a flowchart illustrating the configuration related to the image processing apparatus 300 and a processing procedure of an image processing method according to the fifth embodiment.

For example, as illustrated in FIG. 15, in the fifth embodiment, the image processing circuitry 350 additionally has a removal function 356. The processing circuitry 350 is an example of processing circuitry in the claims.

The removal function 356 removes a non-physical shape included in the three-dimensional CT image data whose analysis conditions are set by the setting function 353. The non-physical shape as used herein means a spatially discontinuous shape or a discontinuous shape between phases. For example, the removal function 356 removes, on the basis of a physical relational expression, a non-physical shape included in the three-dimensional CT image data as a noise.

Specifically, the removal function 356 removes, on the basis of a physical relational expression, a non-physical shape included in the three-dimensional CT image data whose analysis conditions are set by the setting function 353 as a noise. In this case, the removal function 356 uses temporal boundary conditions to perform fluid analysis, thereby deriving a temporal pressure distribution (Step S409). Then, the removal function 356 performs shape smoothing on the vascular shape (Step S410). Specifically, the removal function 356 derives a vascular shape without non-physical discontinuous values on the basis of the derived pressure distribution. The removal function 356 fits the vascular shape having the most reliable phase so as to fulfill the vascular volume in another phase. Steps S409 and S410 are implemented, for example, by the processing circuitry 350 calling and executing a predetermined computer program corresponding to the removal function 356 from the storage circuitry 320. Similarly to the derivation function 355 and the identifying function 354, the removal function 356 also performs fluid analysis by the same processing procedure as in FIG. 11.

This configuration enables non-physical vascular shapes to be corrected, thereby derivation a functional index of the blood vessel more stably and accurately.

The first to the fifth embodiments are described above. In each of the above-mentioned embodiments, an example where the image processing apparatus 300 displays analysis results on the display provided to the image processing apparatus 300 has been described, but the embodiments are not limited thereto. For example, the image processing apparatus 300 may output analysis results to an image display apparatus connected via the network 400.

Some recent image processing systems are built in the form of thin clients, where a client apparatus used by an operator executes the minimum necessary processing and a server apparatus executes the most part of processing. For example, in such an image processing system, the server apparatus may have the function of the image processing apparatus described in the first to the fourth embodiments, and the client apparatus may display analysis results.

In this case, the server apparatus includes at least I/F circuitry, storage circuitry, and processing circuitry. The I/F circuitry is connected to the processing circuitry, and has the same function as that of the I/F circuitry 310 illustrated in FIG. 1. The storage circuitry is connected to the processing circuit, and has the same function as that of the storage circuitry 320 illustrated in FIG. 1. For example, the processing circuitry of the server apparatus has the acquisition function 351, the extraction function 352, the setting function 353, the identifying function 354, and the derivation function 355 illustrated in FIG. 1. In this case, the derivation function 355 transmits a functional index derived as a result of analysis to the client apparatus in response to a request from the client apparatus.

The client apparatus includes at least I/F circuitry, a display, and processing circuitry. The I/F circuitry controls communication between the client apparatus and the server apparatus. The display is connected to the processing circuitry, and has the same function as that of the display 340 illustrated in FIG. 1. For example, the processing circuitry of the client apparatus has a function of acquiring analysis results from the server apparatus and displaying the analysis results on the display.

For example, the processing circuitry of each of the server apparatus and the client apparatus is implemented by a processor. For example, in each of the server apparatus and the client apparatus, each of the above-mentioned processing functions is stored in the storage circuitry in the form of a computer program that can be executed by a computer. Then, the processing circuitry of each of the server apparatus and the client apparatus reads each computer program from the corresponding storage circuitry, and executes the read computer program, thereby implementing the processing function corresponding to the computer program. In other words, the processing circuitry that has read each computer program has each processing function described above.

In each of the above-mentioned embodiments, an example where three-dimensional CT image data collected by the X-ray CT apparatus is used as time-series three-dimensional medical image data in which the blood vessels of the subject are rendered is described. However, the embodiments are not limited thereto. For example, medical images collected by another medical image diagnostic apparatus may be used as time-series three-dimensional medical image data. Examples of the medical image diagnostic apparatus as used herein include an MRI apparatus and an ultrasound diagnostic apparatus.

Sixth Embodiment

Next, a sixth embodiment is described. In the sixth embodiment, an example where the technology disclosed herein is applied to an X-ray CT apparatus is described.

Figure 16:
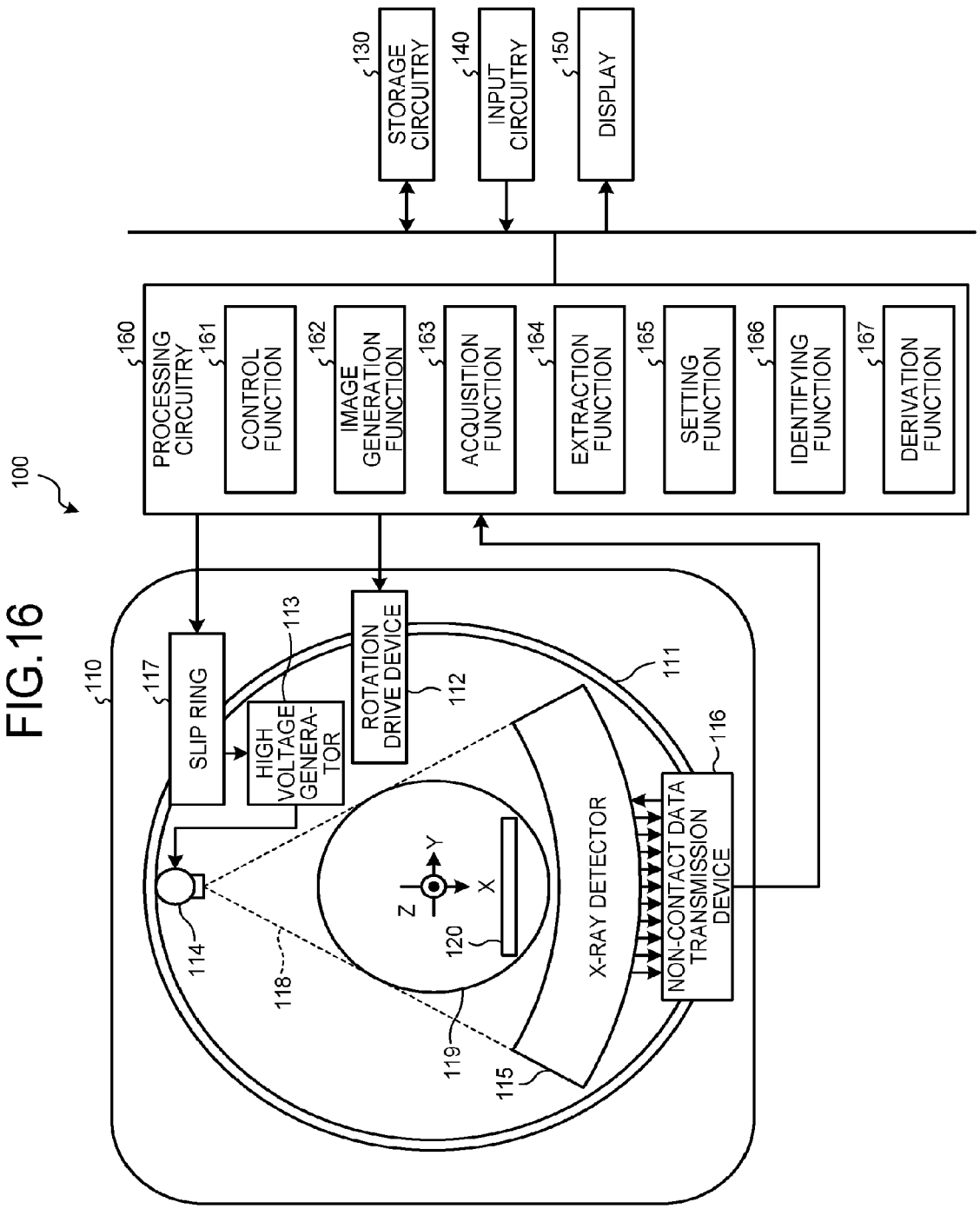
FIG. 16 is a diagram illustrating a configuration example of an X-ray CT apparatus according to a sixth embodiment.

FIG. 16 is a diagram illustrating a configuration example of an X-ray CT apparatus according to the sixth embodiment. For example, as illustrated in FIG. 1, an X-ray CT apparatus 100 according to the sixth embodiment includes a gantry 110, a couchtop 120, storage circuitry 130, input circuitry 140, a display 150, and processing circuitry 160.

The gantry 110 accommodates therein a rotation support mechanism including the rotating frame 111, the rotation drive device 112, and the frame support mechanism. A high voltage generator 113, an X-ray tube 114, an X-ray detector 115, and a non-contact data transmission device 116 are mounted to the rotating frame 111. FIG. 16 omits the illustration of the rotation support mechanism and the frame support mechanism. For example, the gantry 110 is implemented by a gantry formed of metal such as aluminum.

The rotating frame 111 is supported by the frame support mechanism so as to be freely rotatable around the Z-axis, which is a rotation axis set to the X-ray CT apparatus 100. An apparatus coordinate system composed of the X-axis, Y-axis, and Z-axis is set to the X-ray CT apparatus 100. The X-axis is the vertical axis orthogonal to the Z-axis. The Y-axis is the axis orthogonal to the X-axis and the Z-axis.

The rotation drive device 112 drives the rotation of the rotating frame 111. For example, the rotation drive device 112 is implemented by a motor.

The high voltage generator 113 is controlled by the processing circuitry 160 so as to generate a tube voltage to be applied to the X-ray tube 114 and a tube current to be supplied to the X-ray tube 114 on the basis of electric power supplied from the outside of the gantry 110 via a slip ring 117. The high voltage generator 113 may be installed outside the gantry 110. In this case, the high voltage generator 113 applies a tube voltage to the X-ray tube 114 and supplies a tube current to the X-ray tube 114 via the slip ring 117. For example, the high voltage generator 113 is implemented by a high voltage transformer, a filament heating converter, a rectifier, or a high voltage switch.

The X-ray tube 114 radiates an X-ray from a focal spot of the X-ray on the basis of the tube voltage applied from the high voltage generator 113 and the tube current supplied from the high voltage generator 113. A plurality of collimator plates are mounted to an X-ray radiation window provided on the front surface of the X-ray tube 114. Each collimator plate forms the X-ray radiated from the focal spot of the X-ray into a cone beam shape (pyramid). In FIG. 1, the irradiation range of the X-ray is indicated by the broken lines 118. As indicated by the broken lines 118, the X-ray is radiated to the inside of an opening 119 formed in the vicinity of the center of the rotating frame 111 in the gantry 110.

The X-ray detector 115 detects an X-ray transmitted through the subject. Specifically, the X-ray detector 115 includes a plurality of detection elements configured to detect an X-ray. The X-ray detector 115 subjects intensity distribution data on the X-ray detected by the detection elements to amplification, A/D conversion, and other processing to generate raw data, and outputs the generated raw data. For example, the X-ray detector 115 is implemented by an indirect conversion X-ray detector or a direct conversion X-ray detector. In the indirect conversion X-ray detector, for example, the detection elements are formed by a scintillator and an optical sensor such as a photomultiplier tube. Incident X-ray photons are converted into scintillator light by the scintillator, and the converted scintillator light is converted into an electric signal by the optical sensor. In the direct conversion X-ray detector, for example, the detection elements are formed by cadmium telluride (CdTe) based semiconductor elements. Incident X-ray photons are directly converted into an electric signal.

The non-contact data transmission device 116 transmits raw data output from the X-ray detector 115 to the image generation function 162 by a non-contact data transmission method using a magnetic signal or an optical signal. For example, the non-contact data transmission device 116 is implemented by a transmitter, a receiver, and the like provided on the gantry 110 side and a transmitter, a receiver, and the like provided on the rotating frame 111 side. The non-contact data transmission device 116 performs non-contact communications between each transmitter and each receiver to transmit raw data, control signals, and the like. For example, the transmitter transmits an optical signal by a light emitting diode (LED). For example, the receiver receives an optical signal by a photo diode (PD).

The couchtop 120 is used to mount a subject thereon, and is moved along the X-axis, the Y-axis, and the Z-axis by a couchtop drive device (not illustrated). The couchtop drive device is controlled by the processing circuitry 160 to move the couchtop 120 to the inside of an opening 119 formed in the gantry 110.

The storage circuitry 130 stores therein various kinds of data. For example, the storage circuitry 130 stores therein projection data medical images generated by the processing circuitry 160. For example, the storage circuitry 130 is implemented by a semiconductor memory element, such as a random access memory (RAM) and a flash memory, a hard disk, or an optical disc.

The input circuitry 140 receives various kinds of input operations from an operator, converts the received input operations into electric signals, and transmits the electric signals to the processing circuitry 160. For example, the input circuitry 140 receives collection conditions for collecting projection data, reconstruction conditions for reconstructing CT images, image processing conditions for generating processed image from the CT images, and other conditions from the operator. For example, the input circuitry 140 is implemented by a mouse, a keyboard, a trackball, a switch, a button, or a joystick.

The display 150 outputs various kinds of information. For example, the display 150 outputs a medical image generated by the processing circuitry 160 and a graphical user interface (GUI) used to receive various kinds of operations from an operator. For example, the display 150 is implemented by a liquid crystal panel or a cathode ray tube (CRT) monitor.

The processing circuitry 160 controls the overall operation of the X-ray CT apparatus 100 in accordance with the electric signal of the input operation transmitted from the input circuitry 140. For example, the processing circuitry 160 has a control function 161 and an image generation function 162. For example, the processing circuitry 160 is implemented by a processor.

On the basis of collection conditions received from the operator via the input circuitry 140, the control function 161 controls the rotation drive device 112, the high voltage generator 113, the couchtop drive device, and the like to collect projection data on the subject.

The image generation function 162 generates CT image data on the subject on the basis of the X-ray detected by the X-ray detector 115, and stores the generated CT image data in the storage circuitry 130.

Specifically, the image generation function 162 performs preprocessing on raw data transmitted from the non-contact data transmission device 116 to generate projection data, and stores the generated projection data in the storage circuitry 130. For example, the image generation function 162 performs preprocessing such as logarithmic transformation, offset correction, sensitivity correction between channels, and beam hardening correction.

The image generation function 162 performs reconstruction processing on the projection data on the basis of reconstruction conditions transmitted from the input circuitry 140 to reconstruct CT image data on the subject. For example, the image generation function 162 reconstructs three-dimensional CT image data (volume data) by the Feldkamp method or cone-beam reconstruction. For example, the image generation function 162 reconstructs two-dimensional CT image data (tomographic image data) by back projection such as fan-beam reconstruction and filtered back projection (FBP).

The image generation function 162 performs various kinds of image processing on the CT image data on the basis of image processing conditions transmitted from the input circuitry 140, thereby generating various kinds of processed images. For example, the image generation function 162 generates a multi planar reconstruction (MPR) image, a projection image such as a maximum intensity projection (MIP) image, and a volume rendering image.

With the configuration described above, the storage circuitry 130 in the sixth embodiment stores therein correlation information and fluid resistance data similarly to the storage circuitry 320 described in the first or the second embodiment.

In the sixth embodiment, the processing circuitry 160 further has an acquisition function 163, an extraction function 164, a setting function 165, an identifying function 166, and a derivation function 167.

The acquisition function 163 has the same function as the acquisition function 351 described in the first or the second embodiment. While the acquisition function 351 in the first and the second embodiments acquires three-dimensional CT image data from the X-ray CT apparatus 100 or the image storage apparatus 200 via the network 400 and processes the three-dimensional CT image data, the acquisition function 163 according to the sixth embodiment acquires three-dimensional CT image data generated by the image generation function 162 from the storage circuitry 130 and processes the three-dimensional CT image data.

The extraction function 164 has the same function as the extraction function 352 described in the first or the second embodiment. The setting function 165 has the same function as the setting function 353 described in the first or the second embodiment. The identifying function 166 has the same function as the identifying function 354 described in the first or the second embodiment. The derivation function 167 has the same function as the derivation function 355 described in the first or the second embodiment.

In the sixth embodiment, the storage circuitry 130, the input circuitry 140, and the display 150 have the same functions as those of the storage circuitry 320, the input circuitry 330, and the display 340, respectively, described in the first or the second embodiment.

Each processing function included in the processing circuitry 160 is described above. For example, each processing function described above is stored in the storage circuitry 320 in the form of a computer program that can be executed by a computer. The processing circuitry 160 reads each computer program from the storage circuitry 320 and executes the read computer program, thereby implementing the processing function corresponding to each computer program. In other words, the processing circuitry 160 that has read each computer program has each processing function illustrated in FIG. 16.

In FIG. 16, an example where each processing function is implemented by the single processing circuitry 160 is described above. However, the embodiments are not limited thereto. For example, the processing circuitry 160 may be configured by a combination of a plurality of independent processors, and each processing function may be implemented by each processor executing each computer program. Each processing function included in the processing circuitry 160 may be implemented in a manner that the processing functions are appropriately dispersed or integrated in a single processing circuit or a plurality of processing circuits.

The configuration described above enables a functional index of blood vessels to be derived at high speed in a noninvasive or minimally invasive manner even in the sixth embodiment similarly to the first or the second embodiment.

In the above-mentioned sixth embodiment, the processing circuitry 160 has the acquisition function 163, the extraction function 164, the setting function 165, the identifying function 166, and the derivation function 167 similarly to the first or the second embodiment. However, the embodiments are not limited thereto. For example, the X-ray CT apparatus 100 according to the sixth embodiment may exclude the identifying function 166 from the functions of the processing circuitry 160 similarly to the third embodiment. For example, the X-ray CT apparatus 100 according to the sixth embodiment may exclude the setting function 165 and the identifying function 166 from the functions of the processing circuitry 160 similarly to the fourth embodiment.

The first to the sixth embodiments are described above. While an example where the blood vessel of the heart is subjected to analysis is described in each of the above-mentioned embodiments, the embodiments are not limited thereto. The above-mentioned image processing apparatus and X-ray CT apparatus are capable of analyzing blood vessels of any site in human body, such as carotid arteries and cerebral arteries.

In each of the above-mentioned embodiments, an example where the FFR is derived as a functional index is described. However, the embodiments are not limited thereto. The mentioned image processing apparatus and the X-ray CT apparatus are capable of deriving various kinds of functional indices other than the FFR in the same manner.

The term "processor" used in the description of the above-mentioned embodiments means, for example, a central processing unit (CPU), a graphics processing unit (GPU), or circuitry such as an application specific integrated circuit (ASIC) and a programmable logic device (for example, a simple programmable logic device (SPLD), a complex programmable logic device (CPLD), and a field programmable gate array (FPGA)). A computer program may be directly incorporated in circuitry of the processor instead of storing a computer program in the storage circuitry. In this case, the processor implements its functions by reading and executing the computer programs incorporated in the circuitry. Each processor in this embodiment is not limited to the case where each processor is configured as a single circuit, and a plurality of independent circuits may be combined to configure a single processor so as to implement their functions.

A computer program to be executed by the processor is provided by being embedded in a read only memory (ROM), a storage unit, or the like in advance. The computer program may be provided by being recorded in a computer-readable storage medium, such as a compact disc (CD)-ROM, a flexible disk (FD), a CD recordable (CD-R), and a digital versatile disc (DVD), as a file in the format that can be installed or executed by the apparatus. The computer program may be stored on a computer connected to a network such as the Internet, and provided or distributed by being downloaded via the network. For example, the computer program is configured by a module including each functional unit described later. As hardware in practice, a CPU reads and executes a computer program from a storage medium such as a ROM, so that each module is loaded on a main storage device and created on the main storage device.

According to at least one of the embodiments described above, a functional index of a blood vessel can be derived at high speed in a noninvasive or minimally invasive manner.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
   storage circuitry to store therein a fluid resistance database correlating templates of vascular shapes with fluid resistances; and processing circuitry configured to:
- extract, from three-dimensional image data in which a blood vessel of a subject is rendered, vascular shape data representing a shape of the blood vessel;
- divide the vascular shape data into a plurality of segments;
- perform pattern matching between each of the segments of the vascular shape data and the templates included in the fluid resistance database to obtain respective fluid resistances;
- form, based on the obtained fluid resistances, a vascular network expressing one-dimensional fluid resistances; and
- perform fluid analysis by using the formed vascular network to derive a functional index related to a blood circulation state in the blood vessel of the subject.

2. The image processing apparatus according to claim 1, wherein the fluid resistance database stored in the storage circuitry is created from analysis results of analysis using time-series three-dimensional image data in which the blood vessel is rendered.

3. The image processing apparatus according to claim 1, wherein the processing circuitry is further configured to:
- extract, from time-series three-dimensional image data in which a blood vessel of the subject is rendered, time-series vascular shape data representing a shape of the blood vessel; and
- perform the fluid analysis based on the fluid resistance database and the time-series vascular shape data to derive the functional index related to the blood circulation state in the blood vessel of the subject.

4. The image processing apparatus according to claim 1, wherein the processing circuitry is further configured to:
- set analysis conditions including blood physical properties, repeated calculation conditions, analysis initial values, and advance distribution, and eliminate a region with a threshold radius or less in the blood vessel in the vascular shape data to reconstruct a connection relation of the blood vessel; and
- perform the fluid analysis by using the set analysis conditions.

5. The image processing apparatus according to claim 1, wherein the processing circuitry is further configured to:
- identify, based on the three-dimensional image data, pressure boundary conditions at one end of the blood vessel, vascular deformation rigidity, and central venous pressure; and
- perform the fluid analysis by using the boundary conditions to derive the functional index.

6. The image processing apparatus according to claim 1, wherein the fluid resistance database is created from one of analysis results of three-dimensional fluid analysis performed based on blood physical properties and a three-dimensional element model of the blood vessel, and known analysis results.

7. The image processing apparatus according to claim 1, wherein the templates of vascular shapes in the fluid resistance database are each represented by at least one element shape selected from an oval vessel, an expanding vessel, a constricted vessel, a curved vessel, a branch vessel, and a curved diffuser.

8. The image processing apparatus according to claim 1, wherein the fluid resistance database includes, as the templates of vascular shapes, at least one of a cross-sectional area, a flow rate, a flow velocity, a static pressure, a dynamic pressure, a contrast agent concentration, a vorticity, a turbulent intensity, a mean value of shear stress, or coordinates in three-dimensional space for each point on a core line of the blood vessel.

9. The image processing apparatus according to claim 1, wherein the processing circuitry is further configured to form the vascular network based on a core line, a cross-sectional area, and connection information of the blood vessel, and perform the fluid analysis by using the formed vascular network.

10. The image processing apparatus according to claim 1, wherein the processing circuitry is further configured to:
- further analyze, based on the three-dimensional image data, a change in a contrast agent concentration in the blood vessel to acquire a flow velocity in the blood vessel; and
- perform the fluid analysis by further using a flow rate in the blood vessel acquired from the flow velocity in the blood vessel.

11. The image processing apparatus according to claim 10, wherein the processing circuitry is further configured to calculate the flow velocity in the blood vessel by using Expression (1):

$$u = -\frac{\partial(AY)}{\partial t} \Big/ \frac{\partial(AY)}{\partial x} \quad (1)$$

where u is the flow velocity in the blood vessel, t is time, x is a position in the blood vessel, A is a cross-sectional area of the blood vessel, and Y is a contrast agent concentration.

12. The image processing apparatus according to claim 10, wherein the processing circuitry is further configured to calculate the flow velocity in the blood vessel by using Expression (2):

$$u_n = \left[\sum_{j=1}^{n-1}\left\{S_j u_j \left(\frac{\partial Y_i}{\partial x}\right)_j\right\} - S_m u_m \left(\frac{\partial Y_i}{\partial x}\right)_m\right] \Big/ \left\{S_n\left(\frac{\partial Y_i}{\partial x}\right)_n\right\} \quad (2)$$

where u is the flow velocity in the blood vessel, x is a position in the blood vessel, A is a cross-sectional area of the blood vessel, Y is a contrast agent concentration, m is a number of a blood vessel serving as a main vessel, and n is a number of branch vessels connected to the main vessel.

13. The image processing apparatus according to claim 1, wherein the processing circuitry is further configured to:
- remove one of a spatial discontinuous shape and a phase-to-phase discontinuous shape included in the three-dimensional image data; and
- perform the fluid analysis by using three-dimensional image data from which one of the spatial discontinuous shape and the phase-to-phase discontinuous shape is removed.

14. An image processing method, comprising:
- extracting, from three-dimensional image data in which a blood vessel of a subject is rendered, vascular shape data representing a shape of the blood vessel;
- dividing the vascular shape data into a plurality of segments;
- performing pattern matching between each of the segments of the vascular shape data and the templates included in the fluid resistance database to obtain respective fluid resistances;

forming, based on the obtained fluid resistances, a vascular network expressing one-dimensional fluid resistances; and performing fluid analysis by using the formed vascular network to derive a functional index related to a blood circulation state in the blood vessel of the subject.

15. A non-transitory computer readable storage medium including instructions, wherein the instructions, when executed by a computer, cause the computer to perform:

extracting, from three-dimensional image data in which a blood vessel of a subject is rendered, vascular shape data representing a shape of the blood vessel;

dividing the vascular shape data into a plurality of segments;

performing pattern matching between each of the segments of the vascular shape data and the templates included in the fluid resistance database to obtain respective fluid resistances;

forming, based on the obtained fluid resistances, a vascular network expressing one-dimensional fluid resistances; and performing fluid analysis by using the formed vascular network to derive a functional index related to a blood circulation state in the blood vessel of the subject.

* * * * *